United States Patent [19]

Van Lommen et al.

[11] Patent Number: 5,624,952

[45] Date of Patent: Apr. 29, 1997

[54] [(BENZODIOXAN, BENZOFURAN OR BENZOPYRAN) ALKYLAMINO] ALKYL SUBSTITUTED GUANIDINES

[75] Inventors: Guy R. E. Van Lommen, Berlaar; Marcel F. L. De Bruyn, Hoogstraten; Walter J. J. Janssens, Beerse, all of Belgium

[73] Assignee: Janssen Pharmaceutica N.V., Beerse, Belgium

[21] Appl. No.: 632,226

[22] Filed: Apr. 15, 1996

Related U.S. Application Data

[62] Division of Ser. No. 256,995, filed as PCT/EP93/00435, Feb. 19, 1993, Pat. No. 5,541,180.

[30] Foreign Application Priority Data

Feb. 19, 1993 [WO] WIPO ............ PCT/EP93/00435

[51] Int. Cl.⁶ ............... A61K 31/40; C07D 405/06
[52] U.S. Cl. ............... 514/422; 548/525; 548/526
[58] Field of Search ............... 514/422; 548/525, 548/526

[56] References Cited

U.S. PATENT DOCUMENTS

| | | | |
|---|---|---|---|
| 3,166,561 | 1/1965 | Janssen et al. | 260/294 |
| 3,944,549 | 3/1976 | Lafon | 260/256.4 |
| 4,405,622 | 9/1983 | Kluge | 424/250 |
| 4,579,845 | 4/1986 | Cornu et al. | 514/212 |

FOREIGN PATENT DOCUMENTS

| | | |
|---|---|---|
| 4358 | 3/1979 | European Pat. Off. |
| 0387771 | 9/1990 | European Pat. Off. |
| WO83/03607 | 10/1983 | WIPO |
| WO8808-424 | 3/1988 | WIPO |

OTHER PUBLICATIONS

Benkert et al., "Beziehungen zwischen struktur und Noradrenalin–entspeichernder Wirkung von Guanidin– und Amidinderivaten", Arzneim.–Forsch. (Drug Res.) 25, Nr. 9 (1975), 1404–1408.

Manoury et al., "Synthesis and Antihypertensive Activity of a Series of 4–Amino–6,7–dimethoxyquinazoline Derivatives". *J. Med. Chem.*, 1986, 19–25.

*Primary Examiner*—Yogendra N. Gupta
*Attorney, Agent, or Firm*—Charles J. Metz

[57] ABSTRACT

The present invention is concerned with vasoconstricive [(benzodioxan, benzofuran or benzopyran)alkylamino]alkyl substituted guanidines having the formula

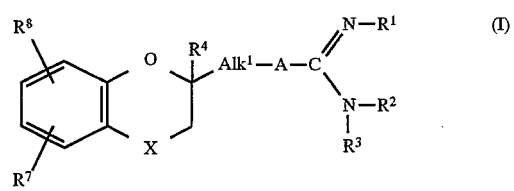

the pharmaceutically acceptable acid addition salts thereof, and the stereochemically isomeric forms thereof, wherein X is O, $CH_2$ or a direct bond; $R^1$ is hydrogen or $C_{1-6}$alkyl; $R^2$ is hydrogen, $C_{1-6}$alkyl, $C_{3-6}$alkenyl or $C_{3-6}$alkynyl; $R^3$ is hydrogen or $C_{1-6}$alkyl; or $R^2$ and $R^3$ may be taken together to form a bivalent radical of formula $-(CH_2)_m-$, wherein m is 4 or 5; or $R^1$ and $R^2$ taken together may form a bivalent radical of formula $-CH=CH-$ or of formula $-(CH_2)_n-$, wherein n is 2, 3 or 4; or $R^3$ may represent a bond when $R_1$ and $R^2$ taken together form a bivalent radical of formula $-CH=CH-CH=$, $-CH=CH-N=$, or $-CH=N-CH=$; $R^4$ is hydrogen or $C_{1-6}$alkyl; $Alk^1$ is a bivalent $C_{1-3}$alkanediyl radical; A is a bivalent radical of formula:

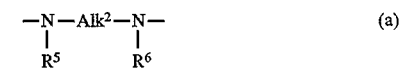

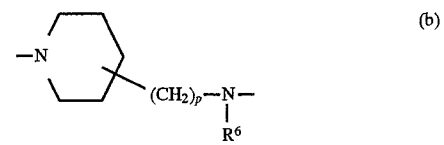

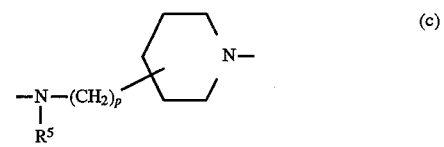

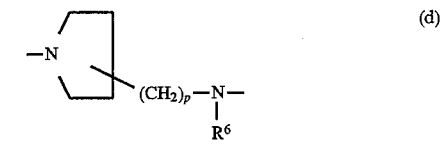

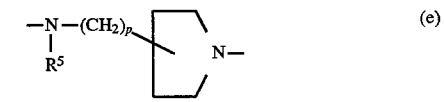

wherein each $R^5$ is hydrogen or $C_{1-4}$alkyl; wherein each $R^6$ is hydrogen or $C_{1-4}$alkyl; $Alk^2$ is $C_{2-15}$alkanediyl or $C_{5-7}$cycloalkanediyl; and each p is 0, 1 or 2; provided that [2-[(2,3-dihydro-1,4-benzodioxin-2-yl)methyl]amino]ethyl guanidine is excluded. Pharmaceuticals which are useful as vasoconstrictors. Compositions comprising said guanidine derivatives as active ingredients, processes for preparing said guanidine derivatives and novel N-cyano guanidine, intermediates; and a use as a medicine are described.

15 Claims, No Drawings

[(BENZODIOXAN, BENZOFURAN OR BENZOPYRAN) ALKYLAMINO] ALKYL SUBSTITUTED GUANIDINES

This application is a division of application Ser. No. 08/256,995, filed Jul. 29, 1994, now U.S. Pat. No. 5,541,180, which was based on PCT application Ser. No. PCT/EP 93/00435, filed Feb. 19, 1993, which claims priority from U.S. patent application Ser. No. 07/842,560, filed Feb. 27, 1992 now abandoned.

BACKGROUND OF THE INVENTION

In EP-0,387,771 there are described benzopyran derivatives which show an inhibitory activity on Maillard reaction and possess an antioxidizing effect. In Arzneim.-Forsch. 25 (9), p. 1404 (1975) there is described [2-[(2,3-dihydro-1,4-benzodioxin-2-yl)methyl]-amino]ethylguanidine in a study concerning noradrenaline depletion effects. In WO-83/03607 a number of cyanoguanidines are described having anti-hypertensive and vasodilator activity. Our novel compounds differ in that they have selective vasoconstrictor activity.

DESCRIPTION OF THE INVENTION

The present invention is concerned with [(benzodioxan, benzofuran or benzopyran)alkylamino]alkyl substituted guanidines having the formula

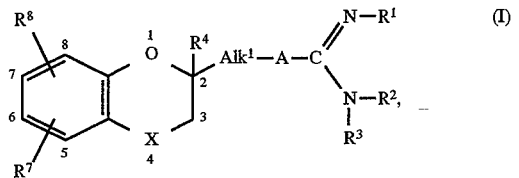

the pharmaceutically acceptable acid addition salts thereof, and the stereochemically isomeric forms thereof, wherein X is O, CH$_2$ or a direct bond;

R$^1$ is hydrogen or C$_{1-6}$alkyl;

R$^2$ is hydrogen, C$_{1-6}$alkyl, C$_{3-6}$alkenyl or C$_{3-6}$alkynyl;

R$^3$ is hydrogen or C$_{1-6}$alkyl; or

R$^2$ and R$^3$ taken together form a bivalent radical of formula —(CH$_2$)$_m$— wherein m is 4 or 5; or R$^1$ and R$^2$ taken together form a bivalent radical of formula —CH=CH— or of formula —(CH$_2$)$_n$—, wherein n is 2, 3 or 4; or R$^3$ may represent a bond when R$^1$ and R$^2$ taken together form a bivalent radical of formula —CH=CH—CH=, —CH=CH—N=, or —CH=N—CH=, wherein one or two hydrogen atoms can be replaced by halo, C$_{1-6}$alkyl, C$_{1-6}$alkyloxy, cyano, amino, mono- or di(C$_{1-6}$alkyl)amino, mono- or di(C$_{3-6}$cycloalkyl)amino, aminocarbonyl, C$_{1-6}$alkyloxycarbonylamino, C$_{1-6}$alkylaminocarbonylamino;

R$^4$ is hydrogen or C$_{1-6}$alkyl;

Alk$^1$ is a bivalent C$_{1-3}$alkanediyl radical;

A is a bivalent radical of formula:

—N—Alk$^2$—N—, (a)
|           |
R$^5$        R$^6$

-continued

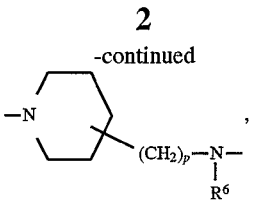
(b)

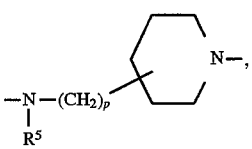
(c)

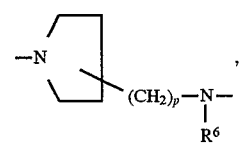
(d)

or

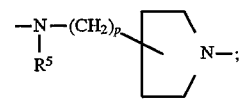
(e)

wherein each R$^5$ is hydrogen or C$_{1-4}$alkyl;
wherein each R$^6$ is hydrogen or C$_{1-4}$alkyl;
Alk$^2$ is C$_{2-15}$alkanediyl or C$_{5-7}$cycloalkanediyl; and each p is 0, 1 or 2; and R$^7$ and R$^8$ each independently are hydrogen, halo, C$_{1-6}$alkyl, C$_{3-6}$alkenyl, C$_{3-6}$alkynyl, hydroxy, C$_{1-6}$alkyloxy, cyano, aminoC$_{1-6}$alkyl, carboxyl, C$_{1-6}$alkyloxycarbonyl, nitro, amino, aminocarbonyl, C$_{1-6}$alkylcarbonylamino, or mono- or di(C$_{1-6}$alkyl) amino; provided that [2-[(2,3-dihydro-1,4-benzodioxin-2-yl)methyl]amino]ethyl guanidine is excluded.

The compounds of formula (I) wherein R$^2$, R$^3$ or R$^6$ are hydrogen may also exist in their tautomeric forms. Such forms although not explicitly indicated in the above formula are intended to be included within the scope of the present invention.

As used in the foregoing definitions halo defines fluoro, chloro, bromo and iodo; C$_{1-4}$alkyl defines straight and branch chained saturated hydrocarbon radicals having 1 to 4 carbon atoms such as, for example, methyl, ethyl, propyl, butyl, 1-methylethyl, 2-methylpropyl and the like; C$_{1-6}$alkyl defines C$_{1-4}$alkyl and the higher homologues thereof having 5 to 6 carbon atoms such as, for example, pentyl, hexyl, 1-methylbutyl and the like; C$_{3-6}$alkenyl defines straight and branch chained hydrocarbon radicals containing one double bond and having from 3 to 6 carbon atoms, such as, for example, 2-propenyl, 3-butenyl, 2-butenyl, 2-pentenyl, 3-pentenyl, 3-methyl-2-butenyl and the like; and the carbon atom of said C$_{3-6}$alkenyl being connected to a nitrogen atom preferably is saturated; C$_{3-6}$alkynyl defines straight and branch chained hydrocarbon radicals containing one triple bond and having from 3 to 6 carbon atoms, such as, for example, 2-propynyl, 3-butynyl, 2-butynyl, 2-pentynyl, 3-pentynyl, 3-hexynyl, and the like; and the carbon atom of said C$_{3-6}$alkynylradical being connected to a nitrogen atom preferably is saturated; C$_{3-6}$cycloalkyl is generic to cyclopropyl, cyclobutyl, cyclopentyl and cyclohexyl; C$_{1-3}$alkanediyl defines bivalent straight and branch chained saturated hydrocarbon radicals having form 1 to 3 carbon atoms, such as, for example, methanediyl, 1,2-ethanediyl, 1,3-propanediyl, 1,2-propanediyl and the like; C$_{2-15}$alkanediyl defines bivalent straight and branch chained saturated hydrocarbon radicals having from 2 to 15 carbon atoms such as, for example, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl, 1,13-tridecanediyl, 1,14-tetradecanediyl, 1,15-pentadecanediyl, and the branched isomers thereof; $C_{5-7}$cycloalkanediyl defines bivalent cyclic saturated hydrocarbon radicals such as, for example, 1,2-cyclopentanediyl, 1,3-cyclopentanediyl, 1,2-cyclohexanediyl, 1,3-cyclohexanediyl, 1,4-cyclohexanediyl, 1,2-cycloheptanediyl, 1,3-cycloheptanediyl, 1,4-cycloheptanediyl.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term addition salt also comprises the hydrates and solvent addition forms which the compounds of formula (I) are able to form. Examples of such forms are e.g. hydrates, alcoholates and the like.

The

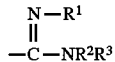

moiety may be acyclic in which case $R^1$ preferably is hydrogen, methyl or ethyl; $R^2$ preferably is hydrogen, methyl, ethyl, propyl or butyl; $R^3$ preferably is hydrogen, methyl or ethyl. Said moiety may also be cyclic in which case it can represent radicals of formula:

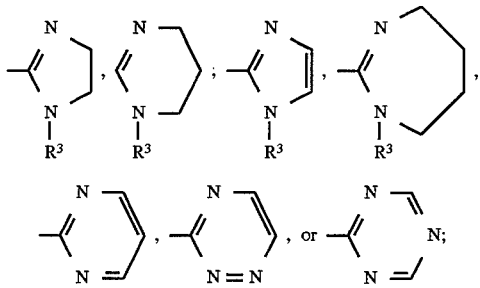

wherein $R^3$ in particular is hydrogen or methyl. The latter cyclic moieties may be unsubstituted or substituted, preferably with halo, especially iodo; $C_{1-6}$alkyl, especially methyl; $C_{1-6}$alkyloxy, especially methoxy; cyano; amino; di$C_{1-6}$alkylamino, especially, dimethylamino; or aminocarbonyl.

Interesting compounds are those compounds of formula (I), wherein $Alk^1$ is —$CH_2$—$CH_2$— or —$CH_2$—, especially —$CH_2$—.

Also interesting are those compounds of formula (I) wherein $R^4$ is hydrogen or $C_{1-4}$alkyl, especially methyl.

Further interesting compounds are those compounds of formula (I) wherein X is $CH_2$ and wherein $R^7$ and $R^8$ each independently are hydrogen; halo, preferably fluoro, chloro or bromo; $C_{1-6}$alkyl, preferably methyl, ethyl, propyl or butyl; $C_{1-6}$alkyloxy, preferably methoxy; hydroxy; cyano; amino; amino$C_{1-6}$alkyl, preferably aminomethyl; $C_{1-6}$alkylcarbonylamino, preferably methylcarbonylamino; or nitro.

Other interesting compounds are those compounds of formula (I) wherein X is O and wherein $R^7$ and $R^8$ each independently are hydrogen; halo, preferably fluoro, chloro, bromo; $C_{1-6}$alkyl, preferably methyl or ethyl; $C_{1-6}$alkyloxy, preferably methoxy; hydroxy, cyano or nitro.

Still other interesting compounds are those compounds wherein X is a direct bond and wherein $R^7$ and $R^8$ each independently are hydrogen, halo, preferably fluoro, chloro or bromo; or $C_{1-6}$alkyl, preferably methyl or ethyl.

Particular compounds are those compounds of formula (I) wherein A represents a radical of formula (a); $Alk^2$ is $C_{2-15}$alkanediyl, especially $C_{2-10}$alkanediyl, more in particular C2–6alkanediyl, preferably 1,3-propanediyl; $R^5$ is hydrogen or methyl; and $R^6$ is hydrogen or methyl.

Further particular compounds are those compounds of formula (I), wherein A represents a radical of formula (b) or (c), p is 0, 1 or 2, especially 0 or 1, preferably 1; and wherein $R^5$ and $R^6$ each independently are hydrogen or methyl.

Particularly interesting are those compounds wherein the absolute configuration of the the carbonatom at the 2-position in formula (I), indicated with an asterisk (*), is as shown in the formula hereunder.

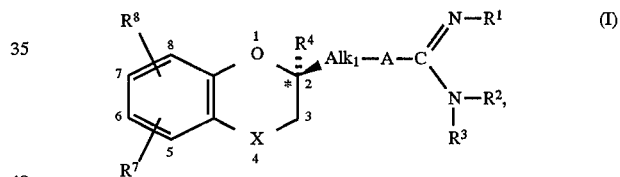

Particularly interesting compounds are those interesting or particular compounds having substituents on the 7- or 8-position (as defined in formula (I)) of the benzodioxan, benzofuran or benzopyran moiety.

Preferred compounds are those compounds of formula (I), wherein X is $CH_2$, $R^7$ and $R^8$ each independently are hydrogen, halo, $C_{1-4}$alkyl, $C_{1-4}$alkyloxy, hydroxy or cyano, especially when substituted on the 7- or 8-position of the benzopyran moiety, and wherein A represents a radical of formula (a), wherein $Alk^2$ represents $C_{2-10}$alkanediyl and $R^5$ and $R^6$ each independently are hydrogen.

Most preferred compounds are N-[(3,4-dihydro-2H-1-benzopyran-2-yl)methyl]-N'-(1,4,5,6-tetrahydro-2-pyrimidinyl)-1,3-propanediamine, the stereochemical isomers thereof, particularly the R-isomer, and the pharmaceutically acceptable acid addition salts thereof.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic saturated hydrocarbon radicals may have either the cis- or trans-configuration and $C_{3-6}$-alkenyl radicals may have the E- or Z-configuration. Stereochemically isomeric forms of the compounds of formula (I) are obviously intended to be embraced within the scope of this invention.

The compounds of formula (I) can generally be prepared by reacting a diamine of formula (II) wherein A, $R^4$, $R^7$ and $R^8$ are as defined under formula (I) with a reagent of formula (III) wherein $R^1$, $R^2$ and $R^3$ are defined under formula (I) and $W_1$ is a reactive leaving group such as, for example, halo, e.g. chloro, bromo; alkyloxy, e.g. methoxy, ethoxy and the like; aryloxy, e.g. phenoxy and the like; alkylthio, e.g. methylthio, ethylthio and the like; arylthio, e.g. benzenethio and the like.

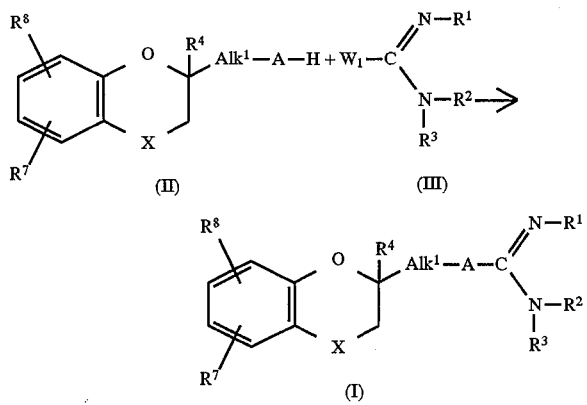

Said reaction can be performed by stirring the diamine of formula (II) with the reagent of formula (III) in an appropriate solvent such as, for example, an alcohol, e.g. methanol, ethanol, propanol and the like; a halogenated hydrocarbon, e.g. dichloromethane, trichloromethane and the like or an ether, e.g. 1,1'-oxybisethane, 2,2'-oxybispropane, tetrahydrofuran, 1,4-dioxane and the like; an aromatic hydrocarbon, e.g. benzene, methylbenzene, dimethylbenzene and the like. Optionally a base, such as, for example, an alkalimetal carbonate, e.g. sodium or potassium carbonate; an alkalimetal hydrogen carbonate, e.g. sodium or potassium hydrogen carbonate; an appropriate organic base, e.g. N,N-diethylethanamine, pyridine, N-(1-methylethyl)-2-propanamine and the like bases, can be added to pick up the acid that may be formed during the course of the reaction. Elevated temperatures may enhance the rate of the reaction. Preferably the reaction is performed at the reflux temperature of the reaction mixture.

The compounds of formula (I) can also generally be prepared by reductive N-alkylation of an aminoderivative of formula (VI) with an appropriate aldehyde of formula (V), wherein r is 0, 1 or 2.

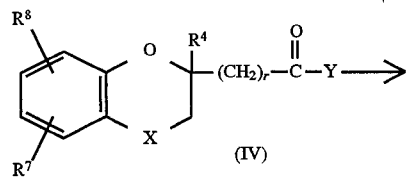

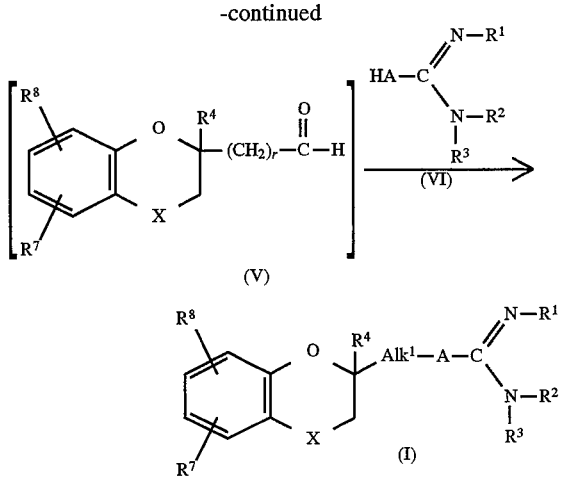

Said reaction is performed by stirring the reactants in an appropriate solvent such as, for example, an alcohol, e.g. methanol, ethanol, propanol and the like; an ether, e.g. 1,1'-oxybisethane, tetrahydrofuran, 1,4-dioxane and the like; an aromatic solvent, e.g. benzene, methylbenzene, dimethylbenzene and the like. Optionally a water separator can be used to remove the water that is formed during the course of the reaction. The resulting imine can then be reduced by catalytic hydrogenation on an appropriate catalyst, such as, for example palladium on charcoal, palladium on bariumsulfate, platinum on charcoal, Raney-Nickel and the like in a suitable solvent, such as, for example an alcohol, e.g. methanol, ethanol and the like; an ether, e.g. tetrahydrofuran, 1,4-dioxane and the like; a carboxylic ester, e.g. ethyl acetate, butyl acetate and the like; or a carboxylic acid, e.g. acetic acid, propanoic acid and the like. Optionally the reaction may be performed at elevated temperatures and/or pressures.

The intermediate aldehyde of formula (V) can, be formed by reducing an acyl derivative of formula (IV) wherein r is defined as above and Y is halo, e.g. chloro, bromo. The acyl halide can be formed by reacting the acid of formula (IV) wherein Y=OH, with a halogenating reagent such as thionylchloride, phosphorus trichloride, phosphorus tribromide, oxalylchloride and the like. The latter reaction may be performed in an excess of the halogenating reagent or in appropriate solvents such as for example halogenated hydrocarbons, e.g. dichloromethane, trichloromethane and the like; aromatic hydrocarbons, e.g. benzene, methylbenzene, dimethylbenzene and the like; ethers, e.g. 1,1'-oxybisethane, tetrahydrofuran, 1,4-dioxane and the like, or dipolar aprotic solvents, e.g. N,N-dimethylformamide, N,N-dimethylacetamide and the like. Stirring and elevated temperatures may be appropriate to enhance the rate of the reaction. Said reduction of the acylhalide of formula (IV) can for instance be perforated by catalytic hydrogenation with a catalyst such as palladium on charcoal, palladium on bariumsulfate, platinum on charcoal and the like in appropriate solvents such as, for example ethers, e.g. 1,1'-oxybisethane, tetrahydrofuran, 1,4-dioxane and the like; preferably in admixture of a dipolar aprotic solvent, such as, for example N,N-dimethylformamide, N,N-dimethylacetamide and the like. Optionally a catalyst poison can be added, such as thiophene, quinoline-sulfur and the like. The reactionsequence starting from the intermediate aldehyde of formula (IV) and yielding compounds of formula (I) may be performed as a one-pot reaction.

The compounds of formula (I) can also be prepared by N-alkylating an amine of formula (VI) with an intermediate of formula (VII), wherein $W_2$ is a reactive leaving group such as, for example, halo, e.g. chloro, bromo or iodo; sulfonyloxy, e.g. methanesulfonyloxy, benzenesulfonyloxy, methylbenzenesulfonyloxy and the like, in appropriate solvents such as ketones, e.g. 2-propanone, 2-butanone and the like; ethers, e.g. 1,1'oxybisethane, tetrahydrofuran, 1,4-dioxane and the like; aromatic hydrocarbons, e.g. benzene, methylbenzene and the like; dipolar aprotic solvents, e.g. N,N-dimethylformamide, N,N-dimethylacetamide, dimethylsulfoxide and the like.

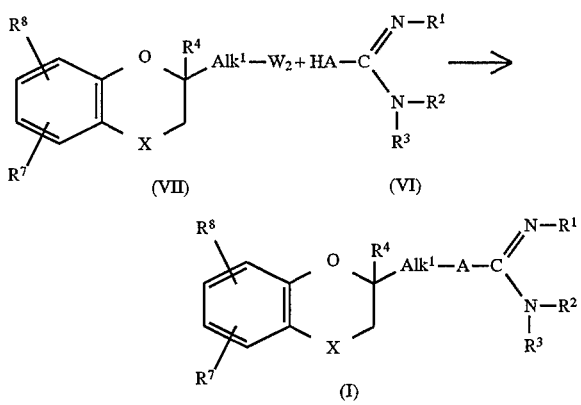

Stirring and heating may enhance the reaction rate. Optionally a suitable base may be added to pick up the acid that is formed during the course of the reaction, such as, for example an alkali metal carbonate, e.g. sodium carbonate, potassium carbonate; an alkali metal hydrogen carbonate, e.g. sodium hydrogen carbonate, potassium hydrogen carbonate and the like; an appropriate organic base, e.g. N,N-diethylethanamine, pyridine and the like.

The compounds of formula (I), wherein A is a bivalent radical of formula (a) and $R^5$ is hydrogen, said compounds being represented by formula (I-a), may be prepared by debenzylation of an intermediate of formula (VIII).

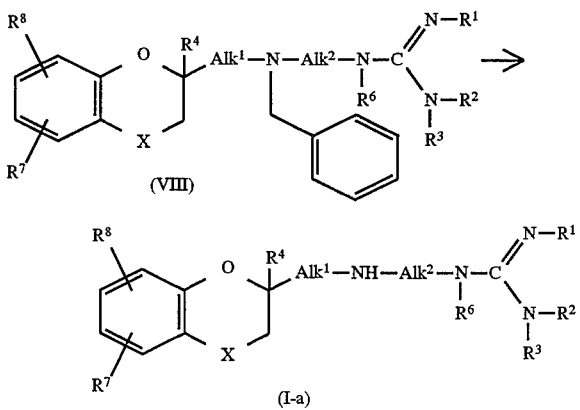

Said debenzylation can be performed following art-known procedures such as catalytic hydrogenation using appropriate catalysts, e.g. platinum on charcoal, palladium on charcoal, in appropriate solvents such as alcohols, e.g. methanol, ethanol, 2-propanol and the like; ethers e.g. 1,1'-oxybisethane, tetrahydrofuran, 2,2'-oxybispropane and the like. Optionally elevated temperatures and pressures may be applied.

The compounds of formula (I) wherein $R^1$ is hydrogen, said compounds being represented by formula (I-b), can be prepared by hydrolysis of the intermediate cyanoguanidines represented by formula (IX-a).

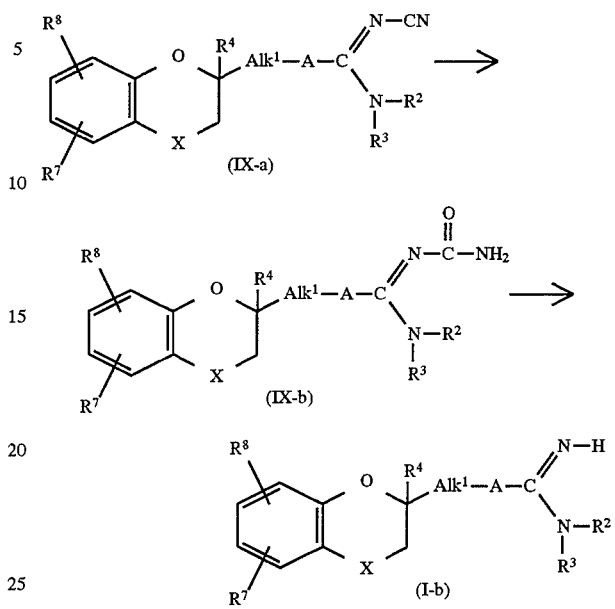

Said hydrolysis can be performed by stirring the intermediate cyanoguanidine of formula (IX-a) in the presence of an acid such as, for example a mineral acid, e.g. hydrochloric acid, hydrobromic acid, sulfuric acid and the like or an organic acid, e.g. acetic acid, formic acid and the like, optionally in admixture with an appropriate solvent such as, for example, an alcohol, e.g methanol, ethanol, propanol and the like; an ether, e.g. 1,1'-oxybisethane, 2,2'-oxybispropane, tetrahydrofuran, 1,4-dioxane and the like. In the course of this hydrolysis the intermediate (IX-b) can be formed. Said intermediate of formula (IX-b) can sometimes be isolated, and further hydrolyzed yielding compounds of formula (I).

The compounds of formula (I), can also be converted into each other by functional group transformations.

For instance the compounds of formula (I), wherein the

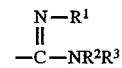

moiety represents a pyrimidinyl moiety, said compounds being represented by formula(I-c), can be converted into the tetrahydroanalogs (I-d) following art-known catalytic hydrogenation procedures.

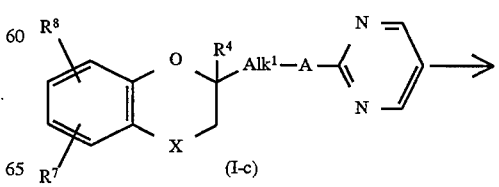

-continued (I-d)

This reduction can be performed simultaneously with the debenzylation mentioned hereinabove in describing the synthesis of the compounds of formula (I-a).

Furthermore, compounds of formula (I) bearing a $C_{3-6}$alkynylgroup or $C_{3-6}$alkenylgroup can be converted into the corresponding compounds bearing $C_{1-6}$alkylgroup following art-known hydrogenation techniques. Compounds of formula (I) bearing a cyanogroup can be converted into the corresponding compounds bearing an aminomethyl substituent following art-known hydrogenation techniques. Compounds bearing an alkyloxy substituent can be converted into compounds bearing a hydroxygroup by treating the alkyloxy compound with an appropriate acidic reagent such as for example, hydrohalic acid, e.g. hydrobromic acid or borontribromide and the like. Compounds bearing an amino substituent can be N-acylated or N-alkylated following art-known N-acylation or N-alkylation procedures.

A number of intermediates and starting materials in the foregoing preparations are known compounds which may be prepared according to art-known methodologies of preparing said or similar compounds and some intermediates are new. A number of preparation methods will be described hereinafter in more detail.

The intermediates of formula (II) wherein A is a radical of formula (a) and $R^6$ is hydrogen, said intermediates being represented by formula (II-a), can be prepared by reducing a nitrile of the formula (X) wherein q is 1 to 14, using art-known reduction conditions. Said reduction can, for instance, be performed by catalytic hydrogenation using an appropriate catalyst, such as, for example, Raney nickel, palladium on charcoal, palladium on bariumsulfate and the like, in an appropriate solvent, such as, for example, an alcohol, e.g. methanol, ethanol, propanol and the like; an ether, e.g. 2,2'-oxybispropane, tetrahydrofuran, 1,4-dioxane and the like, or a mixture of such solvents.

Preferably the reduction is conducted in the presence of ammonia. Optionally higher temperatures or pressures can be applied.

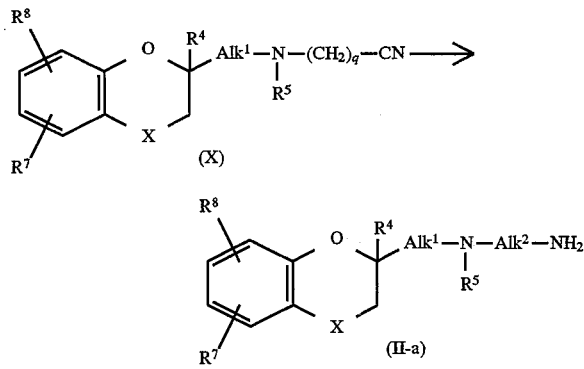

Said reduction can also be carried out by stirring the nitrile with a reducing reagent, such as, for example, borane, lithium aluminum hydride, and the like, in an appropriate solvent, such as an ether, e.g. 2,2'-oxybispropane, tetrahydrofuran, 1,4-dioxane and the like; or a hydrocarbon, e.g. pentane, hexane and the like; an aromatic solvent, e.g. benzene, methylbenzene, dimethylbenzene and the like. Optionally elevated temperatures can be applied to enhance the reaction rate.

The intermediates of formula (X) can be prepared by reacting an amine of formula (XI) with a reagent of formula (XII), wherein $W_2$ and q are defined as hereinabove, in an appropriate solvent such as, for example, a dipolar aprotic solvent, e.g. N,N-dimethylformamide, dimethylsulfoxide, acetonitrile and the like, an aromatic solvent, e.g. benzene, methylbenzene, dimethylbenzene and the like; a ketone, e.g. 2-propanone, 4-methyl-2-pentanone and the like; an ether, e.g. 1,1'-oxybisethane, tetrahydrofuran, 1,4-dioxane and the like.

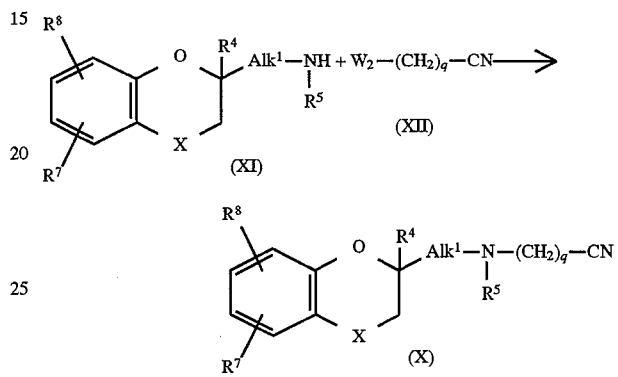

A base as mentioned in the preparation of compounds of formula (I) from intermediates of formula (II) and (III) may be added to pick up the acid that is formed during the course of the reaction. Stirring arid elevated temperatures may enhance the reaction rate. In the formula of the intermediate amine (XI) $R^5$ may also have the meaning of benzyl. This protective group can then be removed in a later stage of the synthesis.

For the preparation of intermediates of formula (X) wherein q=2, said intermediates being represented by formula (X-a) an interesting alternative for the above alkylation comprises stirring the amine of formula (XI) with 2-propenenitrile in an appropriate solvent such as for example, an alcohol, e.g. methanol, ethanol, propanol and the like, an ether, e.g. 1,1'-oxybisethane, tetrahydrofuran, 1,4-dioxan and the like.

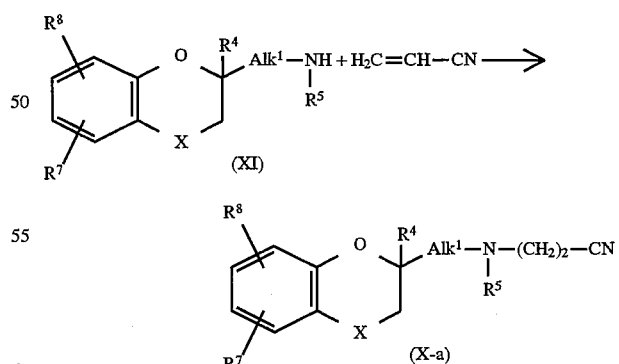

Elevated temperatures may be appropriate to enhance the rate of the reaction. Preferably the reactants are stirred at the reflux temperature of the reaction mixture.

The intermediates of formula (IX-a), wherein $R^4$, $R^7$, $R^8$, X, $Alk^1$ are as defined hereinabove and A is a bivalent radical of formula (a), (c), (d), (e); and wherein $R^2$ is hydrogen, $C_{1-6}$alkyl, $C_{3-6}$alkenyl, or $C_{3-6}$alkynyl, and $R^3$ is hydrogen or $C_{1-6}$alkyl, or $R^2$ and $R^3$ taken together form a bivalent radical of formula $-(CH_2)_m-$, wherein m is 4 or 5, are deemed novel.

The intermediates of formula (IX-a) can be prepared by reacting an intermediate of formula (II) with a reagent of formula (XIII), wherein $W_1$ is a reactive leaving group as defined under formula (III).

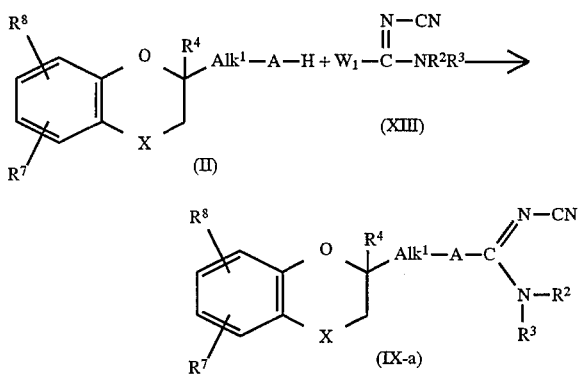

Said reaction can be perforated by stirring the reactants in an appropriate solvent such as an alcohol, e.g. methanol, ethanol and the like, an halogenated hydrocarbon, e.g. dichloromethane, trichloromethane and the like, an aromatic solvent, e.g. benzene, methylbenzene, dimethylbenzene and the like, a dipolar aprotic solvent, e.g. N,N-dimethylformamide, N,N-dimethylacetamide and the like. Optionally a base as mentioned under the preparation of the compounds of formula (I) from intermediates of formula (II) and (III) can be added to pick up the acid that is formed during the course of the reaction. Preferably the reaction is performed at room temperature.

The intermediates of formula (XIII) can be prepared by reacting a cyanamide of formula (XIV) wherein $W_1$ is defined as under formula (III), with an amine of formula (XV).

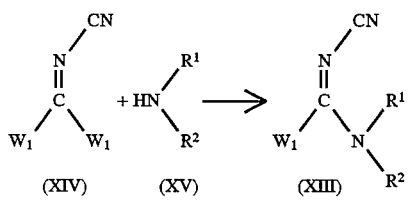

Said reaction can be performed by stirring the reactants in a reaction-inert solvent such as, for example, a halogenated hydrocarbon, e.g. dichloromethane, trichloromethane and the like, an aromatic solvent, e.g. benzene, methylbenzene and the like, an ether, e.g. 1,1'-oxybisethane, tetrahydrofuran, 1,4-dioxane and the like. Optionally a base can be added to pick up the acid that is formed in the course of the reaction. Appropriate bases are alkali metal or earth alkaline metal carbonates or hydrogen carbonates, e.g. sodium carbonate, sodium hydrogen carbonate, potassium carbonate and the like. Elevated temperatures may enhance the reaction rate.

Pure stereochemically isomeric forms of the compounds of this invention may be obtained by the application of art-known procedures. Diastereoisomers may be separated by physical separation methods such as selective crystallization and chromatographic techniques, e.g. liquid chromatography. Enantiomers may be separated from each other by the selective crystallization of their diastereomeric salts with optically active acids. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials. Stereochemically isomeric forms of the compounds of formula (I) are obviously intended to be included within the scope of the invention.

The compounds of formula (I), the pharmaceutically acceptable acid-addition salts and stereochemically isomeric forms thereof have interesting pharmacological properties: they show $5HT_{1-like}$ agonistic activity. The compounds of the present invention have potent and selective vasoconstrictor activity. They are useful to treat conditions which are related to vasodilatation. For instance, they are useful in the treatment of conditions characterized by or associated with cephalic pain, e.g. migraine, cluster headache and headache associated with vascular disorders. These compounds are also useful in the treatment of venous insufficiency and in the treatment of conditions associated with hypotension.

The vasoconstrictor activity of the compounds of formula (I) can be determined using an in vitro-test as is described in "Instantaneous changes of alpha-adrenoreceptor affinity caused by moderate cooling in canine cutaneous veins" in the American Journal of Physiology 234(4), H330–H337, 1978; or in the test described in the pharmacological example, wherein the serotonin-like response of the compounds of the present invention was tested on the basilar arteries of pigs. Novel intermediates of formula (IX-a) as defined hereinabove show similar pharmacological activity.

In view of their useful pharmacological properties, the subject compounds may be formulated into various pharmaceutical forms for administration purposes. To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of the present invention therefore may be used as medicines in conditions related to vasodilatation, more in particular hypotension, venous insufficiency and especially cephalic pain among which migraine. The compounds of the present invention also provide a method of treating warm-blooded animals suffering from conditions related to vasodilatation, such as, hypotension, venous insufficiency and especially cephalic pain among which migraine by administering an effective amount of a compound of formula (I), a pharmaceutically acceptable acid addition salt or a stereoisomeric form thereof. Those skilled in the art could easily determine the effective amount from the test results presented hereinafter. In general it is contemplated that an effective amount would be from 1 µg/kg to 1 mg/kg body weight, and in particular from 2 µg/kg to 200 µg/kg body weight. It may be appropriate to administer the required dose as two, three, four or more sub-doses at appropriate intervals throughout the day. Said sub-doses may be formulated as unit dosage forms, for example, containing 0.005 to 20 mg, and in particular 0.1 mg to 10 mg of active ingredient per unit dosage form.

The following examples are intended to illustrate and not to limit the scope of the present invention in all its aspects.

EXPERIMENTAL PART

A. Preparation of the Intermediates

EXAMPLE 1 a) To a stirred and cooled (0° C.) solution of 32.8 g of 3,4-dihydro-2H-1-benzopyran-2-methanol in 71 ml of pyridine and 135 ml of benzene was added dropwise a solution of 41.9 g of 4-methyl-benzenesulfonyl chloride in 72.5 ml of benzene. Upon completion, stirring was continued for 25 hours. The reaction mixture was washed successively with a hydrochloric acid solution (10%), with water and with a sodium carbonate solution (10%). The organic layer was dried, filtered and evaporated. The residue was purified by column chromatography (silica gel; CHCl$_3$ 100%). The eluent of the desired fraction was evaporated, yielding 28.3 g of 3,4-dihydro-2H-1-benzopyran-2-methanol 4-methylbenzenesulfonate (ester) as a solid residue, mp. 59.4° C. (interm. 1). In a similar way there was also prepared: 6-fluoro-3,4-dihydro-2H-1-benzopyran-2-methanol 4-methylbenzenesulfonate (ester) (interm. 2).

b) A mixture of 7.7 g of intermediate (1), 5.3 g of benzenemethanamine, 5 g of sodium carbonate and 250 ml of 4-methyl-2-pentanone was stirred and refluxed for 48 hours using a water-separator. The reaction mixture was cooled and washed with water. The organic phase was dried, filtered and evaporated. The residue was purified by column chromatography (silica gel; CHCl$_3$/CH$_3$OH 90:10). The eluent of the desired fraction was evaporated and the residue was converted into the ethanedioate salt in ethanol. The salt was filtered off and suspended in 2-propanone. The product was filtered off and dried, yielding 1.16 g (19.5%) of 3,4-dihydro-N-(phenylmethyl)-2H-1-benzopyran-2methanamine ethanedioate (1:1) (interm. 3).

In a similar way there was also prepared:
2,3-dihydro-N-(phenylmethyl)-1,4-benzodioxine-2-methanamine (interm. 4).

EXAMPLE 2

In EP-0.145.067 the synthesis of (+)-6-fluoro-3,4-dihydro-2H-1-benzopyran-2-carboxylic acid (interm. 5) is described.

a) To a stirred and heated (±80° C.) mixture of 49.05 g of intermediate (5) and 244 ml of methylbenzene were added dropwise 54 ml of thionyl chloride during a period of 85 minutes. Upon complete addition, stirring was continued for 2 hours at 80° C. After cooling to room temperature, the reaction mixture was evaporated. The residue was taken up in methylbenzene and the solvent was evaporated again, yielding 60.4 g (100%) of (+)-(S)-6-fluoro-3,4-dihydro-2H-1-benzopyran-2-carbonyl chloride as a residue (interm. 6).

b) A mixture of 46.9 g of intermediate (6) in 60 ml of N,N-dimethylacetamide and 350 ml of 2,2'-oxybispropane was hydrogenated in the presence of 3 g of palladium-oncharcoal catalyst (10%) and 5 ml of a solution of thiophene in methanol (4%). After the calculated amount of hydrogen was taken up, the catalyst was filtered off and the filtrate was added to a mixture of 25 g of benzenemethanamine, 20 g of potassium acetate and 300 ml of methanol. This mixture was hydrogenated again in the presence of 3 g of palladium-on-charcoal catalyst (10%) and 3 ml of a solution of thiophene in methanol (4%). After the calculated amount of hydrogen was taken up, the catalyst was filtered off and the filtrate was evaporated. The residue was poured into water and the whole was basified with NaOH (50%). The product was extracted with dichloromethane and the extract was dried, filtered and evaporated. The residue was purified by column chromatography (silica gel; CH$_2$Cl$_2$/CH$_3$OH 95:5). The eluent of the desired fraction was evaporated and the residue was converted into the hydrochloride salt in 2-propanone by adding 2-propanol saturated with HCl. The salt was filtered off and dried, yielding 46.9 g (69.3%) of (+)-(S)-6-fluoro-3,4-dihydro-N-(phenylmethyl)-2H-1-benzopyran-2-methanamine hydrochloride; mp. 210.7° C.; $[\alpha]_D^{20}$=+92.63° (conc.=0.1% in CH$_3$OH) (interm. 7).

In a similar way there were also prepared:
(S)-3,4-dihydro-N-(phenylmethyl)-2H-1-benzopyran-2-methanamine (interm. 8);
(−)-(R)-6-fluoro-3,4-dihydro-N-(phenylmethyl)-2H-1-benzopyran-2-methanamine hydrochloride; mp. 210.4° C.; $[\alpha]_D^{20}$=−79.47° (conc.=0.1% in CH$_3$OH) (interm. 9);
(R)-3,4-dihydro-N-(phenylmethyl)-2H-1-benzopyran-2-methanamine (interm. 10); and
(±)-3,4-dihydro-2-methyl-N-(phenyhnethyl)-2H-1-benzopyrano2-methanamine (interm 11).

c) A mixture of 28 g of intermediate (10) and 300 ml of methanol was hydrogenated in the presence of 2 g of palladium-on-charcoal catalyst (10%). After the calculated amount of hydrogen was taken up, the catalyst was filtered off and the filtrate was evaporated, yielding 18.2 g (100%) of (−)-(R)-3,4-dihydro-2H-1-benzopyran-2-methanamine as crude residue (interm. 12).

In a similar way there were also prepared:

(±)-2,3-dihydro-1,4-benzodioxine-2-methanamine (interm. 13);

(S)-3,4-dihydro-2H-1-benzopyran-2-methanamine (interm. 14);

(±)-6-fluoro-3,4-dihydro-2H-1-benzopyran-2-methanamine (interm. 15);

(±)-3,4-dihydro-6-methoxy-2H-1-benzopyran-2-methanamine (interm. 16); and (±)-3,4-dihydro-2H-1-benzopyran-2-methanamine (interm. 17).

EXAMPLE 3 a) A mixture of 34 g of ethyl 4-oxo-1-piperidinecarboxylate, 20 g of 2-pyrimidinamine, 8 drops of acetic acid and 103.5 ml of methylbenzene was stirred for 28 hours at reflux temperature using a water-separator. The reaction mixture was evaporated, yielding 50 g of ethyl 4-(2-pyrimidinylimino)-1-piperidinecarboxylate as a residue (interm. 18).

b) To a stirred and cooled (5–10° C.) mixture of 50 g of intermediate (18) in 76 ml of methanol were added portionwise 7.5 g of sodium tetrahydroborate. Upon completion, stirring was continued first for 45 minutes at room temperature and further for 3 hours at reflux temperature. After cooling, the reaction mixture was poured into water and the product was extracted twice with benzene. The combined extracts were washed with water, dried, filtered and evaporated. The residue was solidified in a mixture of 2,2'oxybispropane and 2-propanone. The product was filtered off and crystallized from benzene, yielding 7 g of ethyl 4-(2-pyrimidinylamino)-1-piperidinecarboxylate (interm. 19).

c) A mixture of 7 g of intermediate (19) and 80.5 ml of hydrobromic acid solution (48%) was stirred for 2 hours at reflux temperature. The reaction mixture was evaporated and the residue was taken up in water. The whole was basified with a diluted sodium hydroxide solution, while cooling in an ice-bath. The product was extracted with dichloromethane and the extract was dried, filtered and evaporated. The residue was stirred in 2,2'-oxybispropane. The product was filtered off and converted into the hydrochloride salt in 2-propanol. The salt was filtered off and crystallized from ethanol, yielding 2 g of (±)-N-(4-piperidinyl)-2-pyrimidinamine dihydrochloride hemihydrate; mp. 268.5° C. (interm. 20).

EXAMPLE 4 a) 3 ml of N,N,N-trimethylbenzenemethanaminium hydroxide was added dropwise to a stirred mixture of 60 g (±)-3,4-dihydro-N-(phenylmethyl)-2H-1-benzopyran-2-methanamine in 350 ml of 2-propenenitrile. After stirring for 4 days at reflux temperature, the reaction mixture was cooled and poured into 1,1'-oxybisethane. The whole was filtered over diatomaceous earth and the filtrate was evaporated, yielding 21 g (28.6%) of (±)-3-[[(3,4-dihydro-2H-1-benzopyran-2-yl)methyl](phenylmethyl)amino]propanenitrile as crude residue (interm. 21).

b) A mixture of 21 g of intermediate (21) in 250 ml of methanol was hydrogenated in the presence of 5 g of Raney Nickel. After the calculated amount of hydrogen was taken up, the catalyst was filtered off and the filtrate was evaporated, yielding 20 g (94%) of (±)-N-[(3,4-dihydro-2 H-1-benzopyran-2-yl)methyl]-N-(phenylmethyl)-1,3-propanediamine as crude residue (interm. 22).

c) A mixture of 10 g, of intermediate (22) 4.2 g of 2-chloropyrimidine, 6 g of sodium carbonate and 100 ml of ethanol was stirred and heated for 18 hours. The reaction mixture was cooled and the solvent was evaporated. The residue was treated with water and the product was extracted with 1,1'-oxybisethane. The extract was dried, filtered and evaporated, yielding 11 g (88.5%)of (±)-N-[(3,4-dihydro-2H-1-benzopyran-2yl)methyl]-N-(phenylmethyl)-N'-(2-pyrimidinyl)-1,3-propanediamine as a crude residue (interm. 23).

In a similar way there was also prepared:

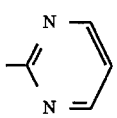

-continued
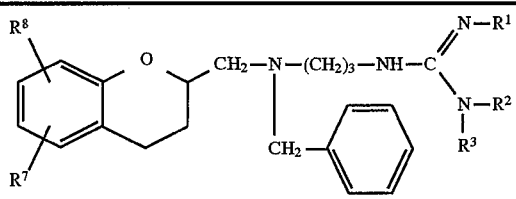
| Int. No. | R7, R8 | R3 | Physical data |
|---|---|---|---|
| 24 | H, H | 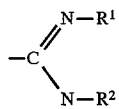 | .2HCl |
| 25 | H, H | 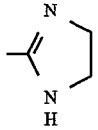 | .HCl; mp. 230.1° C. |
| 26 | H, H | 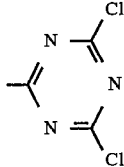 | — |
| 27 | 7-CH2CH3, H | 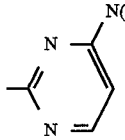 | .2HCl.H2O |
| 28 | H, H | 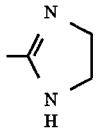 | — |
| 29 | H, H | 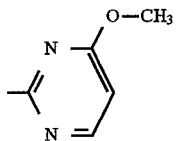 | — |
| 30 | H, H | 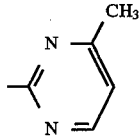 | — |
| 31 | H, H | 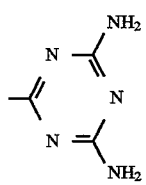 | .2HCl.½H2O; mp. 189.6° C. |

EXAMPLE 5 a) To a stirred solution of 6 g of diphenyl cyanocarbonimidate in 50 ml of dichloromethane at room temperature were added portionwise 2.1 g of piperidine. Stirring was continued for 30 minutes at room temperature. The reaction mixture was evaporated and the residue was crystallized from 2,2'-oxybispropane. The crystals were filtered off and dried, yielding 4.6 g (80.7%) of [phenoxy(1-piperidinyl)methylene]cyanamide; mp. 85.7° C. (interm. 32).

In a similar way was also prepared:

O-phenyl-N'-cyano-N,N-dimethylcarbamimidate (interm. 33).

b) A mixture of 4.0 g of (±)-N-[(3,4-dihydro-2H-1-benzopyran-2-yl)methyl]-1,3-propanediamine, 4.2 g of intermediate (32) and 100 ml of methanol was stirred for 3 days at room temperature. The reaction mixture was evaporated and the residue was dissolved in dichloromethane. This solution was washed with an aqueous $Na_2CO_3$ solution (15%). The organic layer was separated, dried, filtered and evaporated. The residue was purified twice by column chromatography (silica gel; $CH_2Cl_2$/$CH_3OH$ 95:5). The eluent of the desired fraction was evaporated and the residue was converted into the ethanedioate salt (1:1) in 2-propane. The salt was filtered off and recrystallized from methanol. The crystals were filtered off and dried, yielding 1.02 g (12.7%) of (±)-N'-cyano-N-[3-[[(3,4-dihydro-2H-1-benzopyran-2-yl)methyl]amino]propyl]-1-piperidinecarboxidimide ethanedioate (1:1); mp. 176.0° C. (interm. 34).

In a similar way there were also prepared:

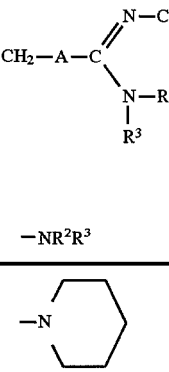

| Int. No. | $R^7$, $R^8$ | X | A | $-NR^2R^3$ | physical data |
|---|---|---|---|---|---|
| 34 | H, H | $CH_2$ | $-NH-(CH_2)_3-NH-$ | 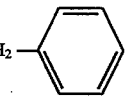 | mp. 176.0° C. ethanedioate (1:1) |
| 35 | 6-F, H | $CH_2$ | $-NH-(CH_2)_3-NH-$ | $-NH-CH_2-CH_3$ | mp. 117.8° C. |
| 36 | H, H | $CH_2$ | $-NH-(CH_2)_3-NH-$ | $-NH-CH_2-CH_3$ | mp. 147.9° C./ ethanedioate (1:1) |
| 37 | H, H | O | $-NH-(CH_2)_3-NH-$ | $-NH-CH_2-CH_3$ | mp. 138.3° C./ ethanedioate (1:1) |
| 38 | H, H | $CH_2$ | $-N-(CH_2)_3-NH-$ with $CH_2$-phenyl substituent on N | $-NH-(CH_2)_2-CH_3$ | — |
| 39 | H, H | $CH_2$ | $-NH-(CH_2)_3-NH-$ | $-NH-CH-(CH_3)_2$ | mp. 121.8° C. |
| 40 | H, H | $CH_2$ | $-NH-(CH_2)_3-NH-$ | $-NH-(CH_2)_2-CH_3$ | mp. 154.6° C./ ethanedioate (1:1) |
| 41 | H, H | $CH_2$ | $-NH-(CH_2)_3-NH-$ | $-N-(CH_3)_2$ | mp. 171.1° C. ethanedioate (1:1) |
| 42 | H, H | $CH_2$ | $-NH-(CH_2)_2-NH-$ | $-NH-CH_3$ | mp. 158.0° C./HCl |
| 43 | H, H | $CH_2$ | $-NH-(CH_2)_3-NH-$ | $-NH-CH_2C\equiv CH$ | mp. 143.2° C. |
| 44 | H, H | $CH_2$ | $-NH-(CH_2)_3-NH-$ | $-NH-CH_2-CH=CH_2$ | mp. 164.7° C. ethanedioate (1:1) |
| 45 | 7-$CH_3$, H | $CH_2$ | $-NH-(CH_2)_3-NH-$ | $-N-(CH_3)_2$ | m.p. 190.2° C. ethanedioate (1:1) |
| 46 | 6-F, H | $CH_2$ | $-NH-(CH_2)_3-NH-$ | $-N-(CH_3)_2$ | m.p. 173.2° C. (−) − (R) ethanedioate (1:1) $[\alpha]_D^{20} = -53.67°$ (c = 1% in DMF) |
| 47 | 7-$CH_2CH_3$, H | $CH_2$ | $-NH-(CH_2)_3-NH-$ | $-N-(CH_3)_2$ | m.p. 137.8° C. ethanedioate (1:1) |
| 48 | 7-$CH_2CH_3$, H | $CH_2$ | $-NH-(CH_2)_3-NH-$ | $-NH-CH_2-CH_3$ | m.p. 91.7° C. |
| 49 | 7-$CH_2CH_3$, H | $CH_2$ | $-NH-(CH_2)_3-NH-$ | $-N-(CH_3)_2$ | m.p. 163.3° C. ethanedioate (1:2) |

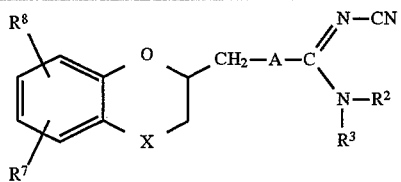

| Int. No. | R⁷, R⁸ | X | A | —NR²R³ | physical data |
|---|---|---|---|---|---|
| 50 | H, H | CH₂ | —N(CH₂)₂—NH— / CH₂—C₆H₅ | —NH—CH₂—CH₃ | mp. 118.5° C. |

EXAMPLE 6

A mixture of 3.1 g (±)-N"-cyano-N-[3-[[(3,4-dihydro-2H-1-benzopyran-2-yl)methyl]amino]propyl]-N'-ethylguanidine in a solution of 10 ml hydrochloric acid in 2-propanol and 50 ml methanol was stirred and refluxed for 30 minutes. The solvent was evaporated. The residue was dissolved in water and this mixture was alkalized with aqueous NaOH (10%). This mixture was extracted with CH₂Cl₂. The organic layer was separated, washed with water, dried (MgSO₄), filtered and the solvent was evaporated. The residue was purified by column chromatography over silica gel (eluent: CH₂Cl₂/CH₃OH/(NH₃)90:10). The pure fractions were collected and the solvent was evaporated. The residue was dissolved in 2-propanol and into the hydrochloric acid salt (1:2) with 2-propanol saturated with HCl. The salt was filtered off and recrystallized from 2-propanol. The crystals were filtered off and dried, yielding 2.95g (±)-N-[[[3-[[(3,4-dihydro-2H-1-benzopyran-2-yl) methyl]amino]propyl]amino](ethylamino)methylene]urea dihydrochloride; mp. 182.2° C. (interm. 51).

In a similar manner there was also prepared:
(±)-N-[[[2-[[(3,4-dihydro-2H-1-benzopyran-2-yl)methyl]amino]ethyl]amino](ethylamino)methylene]urea dihydrochloride; mp. 200.2° C. (interm 52).

EXAMPLE 7 a) A mixture of 12.5 g of 3,4-dihydro-N-(phenylmethyl)-2H-1-benzopyran-2-methanamine, 9 g of 4-bromobutanenitrile, 200 ml of N,N-dimethylformamide and 10 ml of N,N-diethylethanamine was stirred for 72 hour at room temperature. The reaction mixture was evaporated and the residue was partitioned between 1,1'-oxybisethane and water. The organic layer was separated, dried, filtered and evaporated, yielding 11 g (68.7%) of (±)-4-[[(3,4-dihydro-2H-1-benzopyran-2-yl)methyl](phenylmethyl) amino]-butanenitrile (interm. 53).

b) A mixture of 11 g of intermediate (53) and 250 ml tetrahydrofuran was hydrogenated in the presence of 2 g of Raney Nickel. After the calculated amount of hydrogen was taken up, the catalyst was filtered off and the filtrate was evaporated. The residue was partitioned between 1,1'-oxybisethane and water. The organic layer was separated, dried, filtered and evaporated, yielding 10 g (90.6%) of (±)-N-[(3,4-dihydro-2H-1-benzopyran-2-yl)methyl]1-N-(phenylmethyl)-1,4-butanediamine (interm. 54).

c) A mixture of 10 g of intermediate (54), 5.4 g of 2-chloropyrimidine, 8 g of sodium carbonate and 250 ml of ethanol was stirred for 18 hours at reflux temperature. The reaction mixture was evaporated and the residue was partitioned between 1,1'-oxybisethane and water. The organic layer was separated, dried, filtered and evaporated, yielding 10.4 g (83.3%) of (±)-N-[(3,4-dihydro-2H-1-benzopyran-2-yl) methyl]-N-(phenylmethyl)-N'-(2-pyrimidinyl)-1,4-butanediamine (interm. 55).

In a similar way there were also prepared:

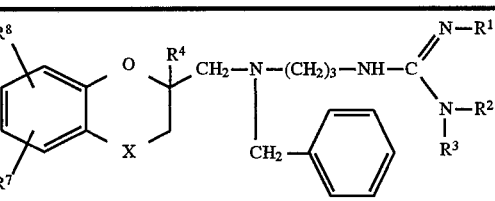

| Int. No. | R⁷, R⁸ | X | R⁴ | n | —C(=N—R¹)NR²R³ | physical data |
|---|---|---|---|---|---|---|
| 55 | H, H | CH₂ | H | 4 | 2-pyrimidinyl | — |

-continued
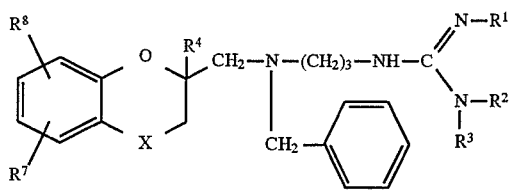
| Int. No. | R⁷, R⁸ | X | R⁴ | n | $-C\underset{NR^2R^3}{\overset{N-R^1}{\parallel}}$ | physical data |
|---|---|---|---|---|---|---|
| 56 | H, H | CH₂ | H | 2 | 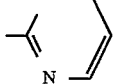 | (S) |
| 57 | 6-F, H | CH₂ | H | 2 | 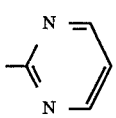 | $[\alpha]_D^{20} = 54.79°$<br>(c = 1% in CH₃OH)<br>mp. 155.9° C./ (+) – (S)<br>2HCl.1/2 H₂O |
| 58 | H, H | CH₂ | H | 2 | 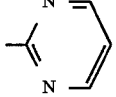 | (R) |
| 59 | 6-F, H | CH₂ | H | 2 | 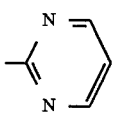 | mp. 173.8° C.<br>(–) – (R) 2HCl |
| 60 | H, H | O | H | 2 | 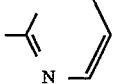 | — |
| 61 | H, H | CH₂ | H | 2 | 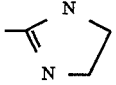 | mp. 175.6° C.<br>2HCl .1/2 H₂O |
| 62 | H, H | CH₂ | CH₃ | 2 | 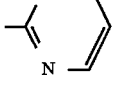 | — |
| 63 | H, H | CH₂ | H | 5 | 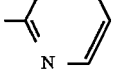 | — |
| 64 | H, H | CH₂ | H | 4 | 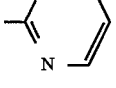 | (R) . HCl |
| 65 | 6-F, H | CH₂ | H | 2 | 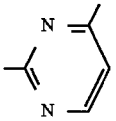 | mp. 219.5° C.<br>(–) – (R).2HCl |

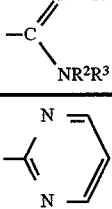

| Int. No. | R⁷, R⁸ | X | R⁴ | n | NR²R³ | physical data |
|---|---|---|---|---|---|---|
| 66 | H, H | CH₂ | H | 5 | (pyridyl) | (R) . HCl |

EXAMPLE 8 a) A mixture of 18 g of intermediate (12), 60 g of 2-propenenitrile and 400 ml of ethanol was stirred for 4 hours at reflux temperature. The reaction mixture was evaporated and the residue was dried, yielding 20 g (84%) of (−)-(R)-3-[[(3,4-dihydro-2H-1-benzopyran-2-yl)methyl]amino]propanenitrile (interm. 67).

b) A mixture of 20 g intermediate (67) and 300 ml of methanol was hydrogenated in the presence of 5 g of Raney Nickel. After the calculated amount of hydrogen was taken up, the catalyst was filtered off and the filtrate was evaporated, yielding 21 g (100%) of (−)-(R)-N-[(3,4-dihydro-2H-1-benzopyran-2-yl)methyl]-1,3-propanediamine as crude residue (interm. 68).

In a similar way there were also prepared:

| Int. No. | R⁷, R⁸ | X |
|---|---|---|
| 68 | H, H | CH₂ |
| 69 | 6-F, H | CH₂ |
| 70 | H, H | O |
| 71 | H, H | CH₂ |
| 72 | 6-OCH₃, H | CH₂ |
| 73 | H, H | CH₂ |

EXAMPLE 9 a) To a stirred mixture of 38.6 g of N,N-dibenzyl-N'-(3,4-dihydro-2H-1-benzopyran-2-yl)-1,2-ethanediamine, 1.2 g of N,N-dimethyl-4-pyridinamine and 300 ml of acetonitrile at room temperature, was added dropwise a solution of 24 g of bis(1,1-dimethylethyl) dicarbonate in 50 ml of acetonitrile. After stirring for 3 hours, the reaction mixture was evaporated and the residue was diluted with water. The product was extracted with 1,1'oxybisethane and the extract was dried, filtered and evaporated, yielding 50 g (100%) of (±)-1,1-dimethylethyl [2-[bis(phenylmethyl) amino ]ethyl][(3,4-dihydro-2H-1-benzopyran-2-yl) methyl]carbamate as crude residue (interm. 74).

b) A mixture of 14.0 g of intermediate (74) and 150 ml of methanol was hydrogenated in the presence of 2 g of palladium-on-charcoal catalyst (10%). After the calculated amount of hydrogen was taken up, the catalyst was filtered off and the filtrate was evaporated. The residue was purified by column chromatography (silica gel; CH₂Cl₂/ CH₃OH(NH₃) 95:5). The eluent of the desired fraction was evaporated, yielding 1.22 g of (±)-1,1-dimethylethyl (2-aminoethyl) [(3,4-dihydro-2H-1-benzopyran-2-yl)methyl]carbamate (interm. 75).

c) To a mixture of 7.0 g of intermediate (75) and 100 ml of trichloromethane were added 3.3 g of dimethyl cyanocarbonimidodithionate. After stirring for 48 hours at reflux temperature, the reaction mixture was evaporated. The residue was purified by column chromatography (silica gel; CH₂Cl₂/CH₃OH 99:1). The eluent of the desired fraction was evaporated, yielding 9.09 g (96.5%) of (±)-1,1-dimethylethyl [2-[[(cyanoimino)-(methylthio) methyl]amino]ethyl][(3,4-dihydro-2H-1-benzopyran-2-yl)methyl]carbamate (interm. 76).

d) To a mixture of 18 g of intermediate (76) and 150 ml of ethanol were added 40 ml of an aqueous solution of ethanamine (70%). After stirring for 16 hours at reflux temperature, the reaction mixture was evaporated and the residue was dissolved in dichloromethane. This solution was washed with water, dried, filtered and evaporated. The residue was purified by column chromatography (silica gel; CH₂Cl₂/CH₃OH 95:5). The eluent of the desired fraction was evaporated and the residue was solidified from 2,2'-oxybispropane, yielding 13.9 g (77.2%) of (±)-1,1-dimethylethyl [2-[[(cyanoimino) (ethylamino)methyl]amino]ethyl][(3,4-dihydro-2H-1-benzopyran-2yl)methyl]carbamate; mp. 115.4° C. (interm. 77).

e) A mixture of 6 g of intermediate (77), 20 ml of 2-propanol saturated with HCl and 200 ml of methanol was stirred for 30 minutes at reflux temperature. The reaction mixture was evaporated and the residue was crystallized from methanol. The product was filtered off and washed with methanol and 2,2'-oxybispropane, yielding 4.3 g (73%) of (±)-N-[[[2-[[(3,4-dihydro-2H-1-benzopyran-2-yl)methyl] amino]ethyl]amino](ethylamino)methylene]urea dihydrochloride; mp. 200.2° C. (interm. 78).

B. Preparation of the Finals

EXAMPLE 10

A mixture of 7.4 g of N¹-[(3,4-dihydro-2H-1-benzopyran-2-yl)methyl]-1,2-ethanediamine, 4.1 g 2-chloropyrimidine, 4.2 g of sodium carbonate and 50.6 ml of ethanol was stirred for 4 hours at reflux temperature. The reaction mixture was evaporated. The residue was purified by column chromatography (silica gel; CHCl$_3$/CH$_3$OH 90:10). The eluent of the desired fraction was evaporated and the residue was converted into the hydrochloride salt in 2-propanol. The salt was filtered off and dried in vacuo, yielding 4.4 g (33.3%) of (±)-N-[(3,4-dihydro-2H-1-benzopyran-2-yl)methyl]-N'-(2-pyrimidinyl)-1,2-ethanediamine dihydrochloride hemihydrate; mp. 192.7° C. (comp. 1).

EXAMPLE 11

A mixture of 8.5 g of 3,4-dihydro-2H-benzopyran-2-carbonyl chloride, 30 ml of N,N-dimethylacetamide and 100 ml of 2,2'-oxybispropane was hydrogenated in the presence of 2 g of palladium-on-charcoal catalyst (10%) and 2 ml of a solution of thiophene in methanol (4%). After the calculated amount of hydrogen was taken up, the catalyst was filtered off and the filtrate was added to a mixture of 5 g of (±)-N$^1$-(2-pyrimidinyl)-1,2-propanediamine and 150 ml of methanol. The whole was hydrogenated in the presence of 2 g of palladium-on-charcoal catalyst (10%) and 5 g of potassium acetate. After the calculated amount of hydrogen was taken up, the catalyst was filtered off and the filtrate was evaporated. The residue was dissolved in 1,1'-oxybisethane, washed with an aqueous NaOH solution, dried, filtered and evaporated. The residue was converted into the ethanedioate salt (1:2) in 2-propanone. The salt was filtered off and dried in vacuo at 60° C., yielding 8.7 g (55.1%) of (±)-N1-[(3,4-dihydro-2H-$^1$-benzopyran-2-yl)methyl]-N$^2$-(2-pyrimidinyl)-1,2-propanediamine ethanedioate(1:2), mp. 150.2° C. (comp. 119).

EXAMPLE 12

A mixture of 4.8g 6-bromo-3,4-dihydro-2H-1-benzopyran-2-carboxaldehyde and 3.1g N-2-pyrimidinyl-1,3-propanediamine in 200ml methanol was hydrogenated with 2g platinum on activated carbon (5%) as a catalyst in the presence of 2ml of a solution of thiophene in methanol (4%). After uptake of H2, the catalyst was filtered off. The filtrate was evaporated. The residue was dissolved in 2-propanone and converted into the ethanedioic acid salt (1:2). The salt was filtered off and recrystallized from ethanol/water. The crystals were filtered off and dried, yielding 2.7g (18.8%) (±)-N-[(6-bromo-3,4-dihydro-2H-1-benzopyran-2-yl)methyl]-N'-(2-pyrimidinyl)-1,3propanediamine ethanedioate(1:2); nap. 215.3° C. (comp. 20).

EXAMPLE 13

A mixture of 3 g N-2-pyrimidinyl-1,3-propanediamine in 150 ml methanol and 10 ml of a solution of hydrochloric acid in 2-propanol was hydrogenated with 2 g palladium on activated charcoal (5%) as a catalyst. After uptake of H$_2$, the catalyst was filtered off. A solution of 4.8 g 6-bromo-3,4-dihydro-2H-1-benzopyran-2-carboxaldehyde in 100ml methanol was added to the filtrate. 10 g Potassium acetate was added and the resulting mixture was hydrogenated with 2 g platinum on activated charcoal (5%) as a catalyst, in the presence of 2 ml of a solution of thiophene in methanol (4%). After uptake of H2, the catalyst was filtered off. The solvent was evaporated and the residue was dissolved in a mixture of H$_2$O/CH$_2$Cl$_2$. This solution was alkalized with NaOH. The organic layer was separated, dried, filtered and the solvent was evaporated. The residue was dissolved in 2-propanone and converted into the ethanedioic acid salt (1:2). The salt was filtered off and dried. This fraction was recrystallized from ethanol/water. The crystals were filtered off and dried, yielding 3.5 g (31.2%) of (±)-N-[(6-bromo-3,4-dihydro-2H-1-benzopyran-2-yl)methyl]-N'-(1,4,5,6-tetrahydro-2-pyrimidinyl)-1,3-propanediamine ethanedioate (1:2); mp. 204.8° C. (comp. 56).

EXAMPLE 14

A mixture of 7.9 g of 3,4-dihydro-2H-1-benzopyran-2-methanol 4-methylbenzenesulfonate(ester), 4.5 g N-(4-piperidinyl)-2-pyrimidinamine, 5.3 g of sodium carbonate and 100 ml of 4-methyl-2-pentanone was stirred overnight at reflux temperature. The reaction mixture was evaporated and the residue was diluted with water. The product was extracted with dichloromethane and the extract was dried, filtered and evaporated. The residue was purified by column chromatography (silica gel; CH$_2$Cl$_2$ 100%). The eluent of the desired fraction was evaporated ,and the residue was crystallized from acetonitrile. The product was filtered off and dried, yielding 28 g (98.8%) of (±)-N-[1-[(3,4-dihydro-2H-1-benzopyran-2-yl)methyl]-4-piperidinyl]-2-pyrimidinamine; mp. 141.9° C. (comp. 128).

EXAMPLE 15

A mixture of 8.4 g of (−)-(R)-N-(6-fluoro-3,4-dihydro-2H-1-benzopyran-2-yl) methyl-N-phenylmethyl-N'-(2-pyrimidinyl)-1,2-ethanediamine and 150 ml methanol was hydrogenated in the presence of 2 g of palladium-on-charcoal catalyst (10%). After the calculated amount of hydrogen was taken up, the catalyst was filtered off and the filtrate was evaporated. The residue was purified by column chromatography (silica gel; CH$_2$Cl$_2$/CH$_3$OH 90:10). The eluent of the desired fraction was evaporated and the residue was crystallized from 2,2'-oxybispropane. The product was filtered off and dried, yielding 3.5 g (55.1%) of (−)-(R)-N-[(6-fluoro-3,4-dihydro-2H-1-benzopyran-2yl)methyl]-N'-(2-pyrimidinyl)-1,2-ethanediamine; mp. 103.2° C. $[\alpha]_D^{20}$=−76.58° (conc.=1% in CH$_3$OH) (comp. 46).

EXAMPLE 16

A mixture of 3.6 g of (−)-(R)-N-[(3,4-dihydro-2H-1-benzopyran-2-yl)methyl]-N'-(2-pyrimidinyl)-1,3-propanediamine dihydrochloride hemihydrate in 150 ml of methanol and 20 ml of 2-propanol saturated with HCl was hydrogenated in the presence of 1.5 g of palladium-on-charcoal catalyst (2%). After the calculated amount of hydrogen was taken up, the catalyst was filtered off and the filtrate was evaporated. The product was crystallized from acetonitrile, filtered off and dried, yielding 2.7 g (74.0%) of (−)-(R)-N-[(3,4-dihydro-2H-1-benzopyran-2-yl)methyl]-N'-(1,4,5,6-tetrahydro-2-pyrimidinyl)-1,3-propanediamine dihydrochloride hemihydrate; mp. 200.2° C. $[\alpha]_D^{20}$=−60.97° (conc. =1% in CH$_3$OH) (comp. 62).

EXAMPLE 17

A mixture of 7.8 g of N-(3,4-dihydro-2H-1-benzopyran-2-yl)methyl-N-phenylmethyl-N'-(2-pyrimidinyl)-1,3-propanediamine, 200 ml methanol and 10 ml of 2-propanol saturated with HCl was hydrogenated in the presence of 2 g of palladium-on-charcoal catalyst (5%). After the calculated amount of hydrogen was taken up, the catalyst was filtered off and the filtrate was evaporated. The residue was converted into the dihydrochloride salt in 2-propanol by adding 2-propanol saturated with hydrochloric acid. The salt was filtered off and dried, yielding 2.9 g (38.0%) of (±)-N-[(3, 4-dihydro-2H-1-benzopyran-2-yl)methyl]-N'-(1,4,5,6-tetrahydro-2-pyrimidinyl)-1,3-propanediamine dihydrochloride; mp. 227.0° C. (comp. 95).

EXAMPLE 18

A solution of 6.9 g of (±)-N-[(3,4-dihydro-6-methoxy-2H-1-benzopyran-2-yl)methyl]-N'-(2-pyrimidinyl)-1,3-propanediamine in 50 ml of dichloromethane was added dropwise to a mixture of 150 ml of a boron tribromide solution in dichloromethane (1M) and 250 ml dichloromethane, stirred under a nitrogen atmosphere at 0° C. The reaction mixture was stirred for 2 hours at room temperature. The resulting precipitate was filtered off and stirred in a mixture of 150 g of ice, 42 g of sodium chloride and 175 ml of $NH_4OH$. Dichloromethane was added and the whole was filtered over diatomaceous earth. The layers were separated and the aqueous layer was extracted with dichloromethane. The combined organic layers were dried, filtered and evaporated. The residue was purified by column chromatography (silica gel; $CH_2Cl_2/CH_3OH/(NH_3)$ 95:5). The eluent of the desired fraction was evaporated and the residue was converted into the ethanedioate salt in 2-propanone. The salt was filtered off and dried in vacuo at 60° C., yielding 3.0 g (28.9%) of (±)-3,4-dihydro-2-[[[3-(2-pyrimidinylamino)propyl]amino]methyl]-2H-1-benzopyran-6-ol ethanedioate (1:2); mp. 170.0° C. (comp. 49).

EXAMPLE 19

A mixture of 2.6 g of (±)-N"-cyano-N-[3-[[(3,4-dihydro-2H-1-benzopyran-2-yl)methyl]amino]propyl]-N'-(1-methylethyl)guanidine in 20 ml of hydrochloric acid 6N was stirred for 2 hours at reflux temperature. The reaction mixture was evaporated and the residue was dissolved in 10 ml of methanol. This solution was filtered and the filtrate was evaporated. The oily residue was dissolved in 10 ml of ethanol. The mixture was filtered and the filtrate was evaporated, yielding 1.32 g (44.4%) of (±)-N-[3-[[(3,4-dihydro-2H-1-benzopyran-2-yl)methyl]amino]propyl]-N'-(1-methylethyl)-guanidine dihydrochloride; mp. 97.5° C. (comp. 150).

EXAMPLE 20

2.3g (±)-N-[(6-fluoro-3,4-dihydro-2H-1-benzopyran-2-yl)methyl]-1,3-propanediamine and 1.6g iodine monochloride were dissolved in 50ml acetic acid. This solution was stirred and refluxed overnight. The solvent was evaporated. The residue was purified by column chromatography over silica gel (eluent: $CH_2Cl_2/CH_3OH$ 99:1 upgrading to 95:5). Two desired fractions were collected and the solvent was evaporated. De residue (±50% pure)was recrystallized from ethanol. The crystals were filtered off and dried, yielding 0.650g (20.1%) of (±)-N-[(6-fluoro-3,4-dihydro-2H-1-benzopyran-2-yl)methyl]-N'-(5-iodo-2-pyrimidinyl)-1,3-propanediamine monohydrochloride; mp. 228.2° C. (comp. 155).

EXAMPLE 21

A mixture of 0.250g palladium on activated carbon 10% in 50ml methanol was stirred under vacuum and rinsed with $H_2$. 5 ml of 2-propanol saturated with HCl was added. A solution of 0.5g (±)-3,4-dihydro-2-[[[3-(2-pyrimidinylamino)propyl]amino]methyl]-2H-1-benzopyran-6-carbonitrile dihydrochloride hemihydrate in 5 ml methanol was added dropwise. The reaction mixture was hydrogenated while stirring for 2 hours. After uptake of H2, the mixture was filtered over dicalite.

The filter residue was washed with $CH_3OH$. The filtrate was evaporated and the residue was stirred in 10ml $CH_3OH$, filtered over a pleated paper filter and washed with 5ml $CH_3OH$. The filtrate was evaporated. The residue was stirred in 10 ml 2-propanone, then filtered over a glass filter. The filter residue was dried, yielding 0.427g (82.2%); mp. 240.1° C. (comp. 102).

EXAMPLE 22

50 ml Methylbenzene was added to 4.3 g (±)-methyl 8-ethynyl-6-fluoro-3,4-dihydro-2H-1-benzopyran-2-carboxylate, then evaporated. The residue was dissolved in 100 ml methylbenzene and this solution was cooled to –70° C. A solution of 25 ml hydrobis(2methylpropyl)aluminum hydride in methylbenzene (20%) was added dropwise. The reaction mixture was stirred for 1 hour at –70° C. 10 ml Methanol was added dropwise and the temperature was allowed to reach room temperature. The reaction mixture was poured out into 150 ml water and extracted with diethyl ether. The separated organic layer was dried, filtered and the solvent was evaporated. The residue was dissolved in methanol and 1.95 g N-(2-pyrimidinyl)-1,3-propanediamine was added. This mixture was hydrogenated at room temperature with 1 g palladium on activated carbon (10%) as a catalyst in the presence of a solution of 4 ml of thiophene (4%). After uptake of $H_2$, the catalyst was filtered off. The filtrate was evaporated. The residue was purified by column chromatography over silica gel (eluent: $CH_2Cl_2/CH_3OH$ 95:5 upgrading to 90:10). The pure fractions were collected and the solvent was evaporated. The residue was dissolved in 80 ml 2-propanone and converted into the ethanedioic acid salt (1:1). The salt was filtered off, washed with 2opropanone and 2,2'-oxybispropane, then dried, yielding 4.3 g (63.1%) of (±)-N-[(8-ethyl-6-fluoro-3,4-dihydro-2H-1-benzopyran-2-yl)methyl]-N'-2-pyrimidinyl-1,3-propanediamine ethanedioate (1:2); mp. 210.8° C. (comp. 54).

All compounds listed in Tables 1 to 5 were prepared following methods of preparation described in Examples 10 to 22, as indicated in the column Ex. No.

TABLE 1

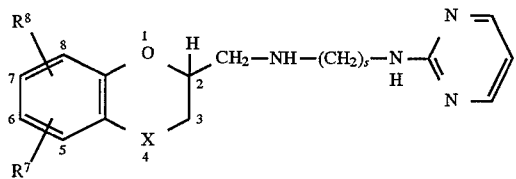

| Co. No. | Ex. No. | R⁷ | R⁸ | X | s | physical data |
|---|---|---|---|---|---|---|
| 1 | 10 | H | H | CH₂ | 2 | mp. 192.7° C./. 2 HCl .½ H2O |
| 2 | 10 | H | H | CH₂ | 3 | mp. 193.4° C./[α]$_D^{20}$ = −63.46° (c = 1% in CH₃OH) (−) − (R).2 HCl . ½H₂O |
| 3 | 10 | 6-F | H | CH₂ | 3 | mp. 139.9° C./ .2 HCl . ½H₂O |
| 4 | 10 | H | H | O | 3 | — |
| 5 | 10 | H | H | CH₂ | 3 | mp. 223.2° C./[α]$_D^{20}$ =48.63° (c = 0.1% in CH₃OH)/(+) − (S) . HCl |
| 6 | 10 | 6-O—CH₃ | H | CH₂ | 3 | mp. 190.6° C./. HCl |
| 7 | 10 | 7-CH₃ | H | CH₂ | 3 | mp. 212.0° C./ethanedioate (1:2) |
| 8 | 10 | 7-C₂H₅ | H | CH₂ | 3 | mp. 141.4° C./[α]$_D^{20}$ = 67.48° (c = 1% in CH₃OH)/(+) − (S) .2 HCl . ½ H₂O |
| 9 | 10 | 7-C₂H₅ | H | CH₂ | 3 | mp. 154.9° C./[α]$_D^{20}$ = −69.37° (c = 1% in CH₃OH)/(−) − (R) .2 HCl |
| 10 | 11 | H | H | — | 3 | mp. 145.8 C./ .2 HCl . ½ H₂O |
| 11 | 11 | 6-F | H | CH₂ | 6 | mp. 170.3 C./ . 2HCl |
| 12 | 11 | 6-F | H | CH₂ | 3 | mp. 197.5° C./(+) − (S) .2 HCl |
| 13 | 11 | 6-F | H | CH₂ | 3 | mp. 200.9° C./(−) − (R) .2 HCl |
| 14 | 11 | 6-F | H | CH₂ | 4 | mp. 171.1° C./[α]$_D^{20}$ = −64.54° (c = 1% in CH₃OH)/(−) − (R) .2 HCl |
| 15 | 11 | 6-F | H | CH₂ | 4 | mp. 177.4° C./[α]$_D^{20}$ = 66.26° (c = 1% in CH₃OH)/(+) − (S) .2 HCl |
| 16 | 11 | 7-C₂H₅ | H | CH₂ | 3 | mp. 125.5° C./ .2 HCl . ½H₂O |
| 17 | 11 | 7-C₂H₅ | H | CH₂ | 5 | mp. 177.1° C./ .2 HCl |
| 18 | 11 | 7-C₂H₅ | H | CH₂ | 4 | mp. 140.1° C./ .2 HCl |
| 19 | 11 | H | H | O | 4 | mp. 208.1° C./ethanedioate (1:1) |
| 20 | 12 | 6-Br | H | CH₂ | 3 | mp. 215.3° C./ethanedioate (1:2) |
| 21 | 12 | 6-CH₃ | H | CH₂ | 3 | mp. 207.1° C./ethanedioate (1:1) |
| 22 | 12 | 7-F | H | CH₂ | 3 | mp. 217.3° C./ethanedioate (1:1) |
| 23 | 12 | 5-CH₃ | 7-CH₃ | CH₂ | 3 | mp. 186.6° C./. 2 HCl |
| 24 | 12 | H | 8-OCH₃ | CH₂ | 3 | mp. 216.1° C./. 2 HCl |
| 25 | 12 | H | H | CH₂ | 9 | mp. 159.7° C./ 2 HCl . ½ H₂O |
| 26 | 12 | H | H | CH₂ | 8 | mp. 152.9° C./ 2 HCl |
| 27 | 12 | 7-OCH₃ | H | CH₂ | 3 | ethanedioate (1:1) |
| 28 | 12 | H | H | CH₂ | 10 | mp. 164.9° C./.2 HCl |
| 29 | 12 | H | H | CH₂ | 7 | mp. 152.4° C./.2 HCl |
| 30 | 12 | 6-F | 8-Br | CH₂ | 3 | mp. 145.0° C. |
| 31 | 12 | H | 8-CH₃ | CH₂ | 3 | ethanedioate (1:2) |
| 32 | 12 | 5-OCH₃ | H | CH₂ | 3 | mp. 219.9° C./ethanedioate (1:1) |
| 33 | 12 | H | 8-CH₃ | CH₂ | 3 | mp. 219.3° C./ethanedioate (1:1) |
| 34 | 12 | 7-CH(CH₃)₂ | H | CH₂ | 3 | mp. 127.0° C./. 2 HCl . H₂O |
| 35 | 12 | 7-C₄H₉ | H | CH₂ | 3 | mp. 170.9° C./. 2 HCl . H₂O |
| 36 | 12 | 7-C₃H₇ | H | CH₂ | 3 | .2 HCl . 2 H₂O |
| 37 | 12 | 7-C(CH₃)₃ | H | CH₂ | 3 | .2 HCl |
| 38 | 12 | 7-CH₃ | 8-CH₃ | CH₂ | 3 | .2 HCl |
| 39 | 12 | H | H | CH₂ | 3 | mp. 120.9° C./[α]$_D^{20}$ = −15.78° (c = 1% in methanol)/ (−) − (R) cyclohexylsulfamate (1:2) |
| 40 | 12 | 6-F | 8-NHCOCH₃ | CH₂ | 3 | mp. 172.9° C./ethanedioate (1:2) |
| 41 | 14 | 6-CN | H | CH₂ | 3 | mp. 175.1° C./. 2 HCl . ½ H₂O |
| 42 | 14 | 6-Br | 8-NO₂ | CH₂ | 3 | mp. 195.1° C./ .2 HCl |
| 43 | 15 | H | H | CH₂ | 2 | mp. 201.7° C./[α]$_D^{20}$ = 89.14° (c = 1% in CH₃OH)/ (+) − (S) . 2 HCl |
| 44 | 15 | 6-F | H | CH₂ | 2 | mp. 102.9° C./[α]$_D^{20}$ = 80.32° (c = 1% in CH₃OH)/ (+) − (S) |
| 45 | 15 | H | H | CH₂ | 2 | mp. 204.5° C./[α]$_D^{20}$ = −63.45° (c = 0.5% in DMF)/ (−) − (R) . 2 HCl |
| 46 | 15 | 6-F | H | CH₂ | 2 | mp. 103.2° C./[α]$_D^{20}$ = −76.58° (conc. = 1% in CH₃OH)/ (−) − (R) |
| 47 | 15 | H | H | CH₂ | 3 | mp. 142.9° C./ .2 HCl . ½ H₂O |
| 48 | 15 | H | H | CH₂ | 4 | mp. 140.8° C./.2 HCl . H₂O |
| 49 | 18 | 6-OH | H | CH₂ | 3 | mp. 170.0° C./ethanedioate (1:2) |
| 50 | 18 | H | 8-OH | CH₂ | 3 | mp. 170.5° C./ . 2 HCl |
| 51 | 18 | 7-OH | H | CH₂ | 3 | — |
| 52 | 18 | 5-OH | H | CH₂ | 3 | mp. 139.1° C./ethanedioate (1:2) |

TABLE 1-continued

[Structure: Benzene ring with R8 at position 8, R7 at position 5-7, O at position 1, X at position 4, connected via CH-CH2-NH-(CH2)s-NH-C(=N)-pyrimidine ring]

| Co. No. | Ex. No. | R⁷ | R⁸ | X | s | physical data |
|---------|---------|-----|--------------|-----|---|----------------|
| 53 | 21 | H | 8-NH₂ | CH₂ | 3 | mp. 270.7° C./ .3 HCl . H₂O |
| 54 | 22 | 6-F | 8-CH₂—CH₃ | CH₂ | 3 | mp. 210.8° C./ethanedioate (1:2) |

TABLE 2

[Structure: Benzene ring with R8 at position 8, R7 at position 5-7, O at position 1, X at position 4, connected via CH-CH2-NH-(CH2)s-NH-C(=N)-tetrahydropyrimidine ring with NH]

| Co No | Ex No | R⁷ | R⁸ | X | s | physical data |
|-------|-------|-----|-----|-----|---|----------------|
| 55 | 10 | 6-OCH₃ | H | CH₂ | 3 | mp. 199.9° C./ . 2 HBr |
| 56 | 13 | 6-Br | H | CH₂ | 3 | mp. 204.8° C./ ethanedioate (1:2) |
| 57 | 16 | H | H | CH₂ | 2 | mp. 216.7° C./ . 2 HCl |
| 58 | 16 | H | H | CH₂ | 2 | mp. 197.8° C./ [α]$_D^{20}$ = 53.59° (c = 0.5% in CH₃OH)/ (+) − (S). 2 HCl |
| 59 | 16 | H | H | CH₂ | 2 | mp. 199.2° C./ [α]$_D^{20}$ = −52.66° (c = 0.5% in DMF)/ (−) − (R). 2 HCl |
| 60 | 16 | 6-F | H | CH₂ | 2 | mp. 215.1° C./ [α]$_D^{20}$ = 68.31° (c = 1% in CH₃OH)/ (+) − (S). 2 HCl |
| 61 | 16 | 6-F | H | CH₂ | 2 | mp. 213.19° C./ [α]$_D^{20}$ = −64.80° (c = 1% in CH₃OH)/ (−) − (R). 2 HCl |
| 62 | 16 | H | H | CH₂ | 3 | mp. 200.2° C./ [α]$_D^{20}$ = −60.97° (c = 1% in CH₃OH) (−) − (R) . 2HCl . ½ H₂O |
| 63 | 16 | 6-F | H | CH₂ | 3 | mp. 226.3° C./ . 2 HCl |
| 64 | 16 | H | H | O | 3 | mp. 164.7° C./ . 2 HCl |
| 65 | 16 | H | H | CH₂ | 3 | mp. 162.0° C./ [α]$_D^{20}$ = 65.83° (c = 1% in CH₃OH) (+) − (S) . 2 HCl . H₂O |
| 66 | 16 | H | H | — | 3 | mp. 167.9° C./ . 2 HCl . ½ H₂O |
| 67 | 16 | 7-CH₃ | H | CH₂ | 3 | mp. 216.4° C./ethanediaote (1:2) |
| 68 | 16 | 6-F | H | CH₂ | 6 | mp. 201.1° C./ .2 HCl |
| 69 | 16 | 6-F | H | CH₂ | 3 | mp. 228.9° C./ [α]$_D^{20}$ = 65.47° (c = 1% in CH₃OH) .(+) − (S) . 2 HCl |
| 70 | 16 | 6-F | H | CH₂ | 3 | mp. 228.9° C./ [α]$_D^{20}$ = −65.45° (c = 1% in CH₃OH) (−) − (R). 2 HCl |
| 71 | 16 | 6-F | H | CH₂ | 4 | mp. 203.2° C./ [α]$_D^{20}$ = 65.81° (+) − (S) . 2 HCl |
| 72 | 16 | 7-F | H | CH₂ | 3 | mp. 221.2° C./ ethanedioate (1:2) |
| 73 | 16 | 7-CH₂—CH₃ | H | CH₂ | 3 | mp. 155.3° C./ .2 HCl. ½H₂O |
| 74 | 16 | 5-CH₃ | 7-CH₃ | CH₂ | 3 | mp. 195.4° C./ . 2 HCl |
| 75 | 16 | H | H | CH₂ | 9 | mp. 154.6° C./ . 2HCl |
| 76 | 16 | H | 8-OCH₃ | CH₂ | 3 | mp. 130.0° C./ . 2 HCl. ½ H₂O |
| 77 | 16 | H | H | CH₂ | 8 | mp. 139.5° C./ . 2 HCl. ½ H₂O |
| 78 | 16 | H | 7-OCH₃ | CH₂ | 3 | mp. 213.6° C./ ethanedioate (1:2) |
| 79 | 16 | H | H | CH₂ | 10 | mp. 132.3° C./ . 2 HCl. ½ H₂O |
| 80 | 16 | H | H | CH₂ | 7 | mp. 113.0° C./ . 2 HCl. ½ H₂O |
| 81 | 16 | 7-CH₂—CH₃ | H | CH₂ | 4 | mp. 157.2° C./ .2 HCl |
| 82 | 16 | 7-CH₂—CH₃ | H | CH₂ | 5 | mp. 125.1° C./ .2 HCl |
| 83 | 16 | 6-OH | H | CH₂ | 3 | mp. 241.3° C./ .2 HCl |
| 84 | 16 | H | 8-CH₃ | CH₂ | 3 | mp. 183.8° C./ ethanedioate (1:2) |
| 85 | 16 | 5-OCH₃ | H | CH₂ | 3 | mp. 183.2° C./ ethanedioate (1:2) |
| 86 | 16 | 7-CH(CH₃)₂ | H | CH₂ | 3 | mp. 171.0° C./ . 2 HCl. ½ H₂O |
| 87 | 16 | 7-C₄H₉ | H | CH₂ | 3 | mp. 178.2° C./ . 2 HCl |
| 88 | 16 | 7-C₃H₇ | H | CH₂ | 3 | mp. 161.2° C./ . 2 HCl. ½ H₂O |

TABLE 2-continued

[Structure: chromane with R8 at position 8, R7 at position 5, X at position 4, with -CH2-NH-(CH2)s-NH-C(=N-)-NH- linked to tetrahydropyrimidine ring]

| Co No | Ex No | R⁷ | R⁸ | X | s | physical data |
|---|---|---|---|---|---|---|
| 89 | 16 | 7-C(CH₃)₃ | H | CH₂ | 3 | mp. 191.5° C./ . 2 HCl . H₂O |
| 90 | 16 | 7-CH₃ | 8-CH₃ | CH₂ | 3 | mp. 202.7° C./ . 2 HCl . H₂O |
| 91 | 16 | H | H | CH₂ | 3 | mp. 165.9° C./ $[\alpha]_D^{20}$ = −26.40° (c = 1% in methanol)/ (−) − (R) cyclohexylsulfamate (1:2) |
| 92 | 16 | 7-C₂H₅ | H | CH₂ | 3 | mp. 172.9° C./ $[\alpha]_D^{20}$ = −76.83° (c = 1% in methanol)/ (−) − (R) .2 HCl |
| 93 | 16 | 6-F | 8-NHCOCH₃ | CH₂ | 3 | mp. 202.2° C./ ethanedioate (1:2) |
| 94 | 16 | 6-F | 8-C₂H₅ | CH₂ | 3 | mp. 204.1° C./ ethanedioate (1:2) |
| 95 | 17 | H | H | CH₂ | 3 | mp. 227.0° C./ . 2 HCl |
| 96 | 17 | H | H | O | 2 | mp. 220.8° C./ . 2 HCl |
| 97 | 17 | H | H | CH₂ | 4 | mp. 96.2° C./ . 2 HCl . ½ H₂O |
| 98 | 17 | H | H | CH₂ | 5 | mp. 157.5° C./ . 2 HCl . ½ H₂O |
| 99 | 17 | H | H | CH₂ | 4 | mp. 117.5° C./ $[\alpha]_D^{20}$ = −62.87° (c = 1% in CH₃OH) (−) − (R) 2 HCl .½H₂O |
| 100 | 17 | H | H | CH₂ | 5 | mp. 191.8° C./ $[\alpha]_D^{20}$ = −59.92° (c = 1% in CH₃OH) (−) − (R) 2 HCl .½ H₂O |
| 101 | 17 | 6-F | H | CH₂ | 4 | mp. 209.5° C./ $[\alpha]_D^{20}$ = −63.68° (−) − (R) 2 HCl |
| 102 | 21 | 6-CH₂—NH₂ | H | CH₂ | 3 | mp. 240.1° C./ 3 HCl . ½ H₂O |

TABLE 3

| Co. No. | Ex. No. | R⁷ | R⁸ | X | —CH₂—A— | R³ group | physical data |
|---|---|---|---|---|---|---|---|
| 103 | 10 | H | H | CH₂ | —NH—(piperidine)—N— | pyridyl | mp. 264.2° C./ .2 HCl |
| 104 | 10 | H | H | CH₂ | —N(CH₃)—(CH₂)₂—NH— | pyridyl | mp. 219.2° C./ .2 HCl |
| 105 | 10 | H | H | CH₂ | —N(piperidine)—CH₂—NH— | pyridyl | mp. 121.6° C. |

TABLE 3-continued

| Co. No. | Ex. No. | R⁷ | R⁸ | X | —CH₂—A | R³ (of C(=N-R¹)N(R²)R³) | physical data |
|---|---|---|---|---|---|---|---|
| 106 | 10 | 6-F | H | CH₂ | —N(H)—(CH₂)₃—N(H)— | 4,5-dihydro-1H-imidazol-2-yl (N-H) | mp. 201.0° C./ .2 HCl |
| 107 | 10 | H | H | CH₂ | trans-1,3-cyclohexanediyl bis-NH— | pyrimidin-2-yl | mp. 220.4° C. .2 HCl. 1/2 H₂O trans |
| 108 | 10 | H | H | CH₂ | cis-1,3-cyclohexanediyl bis-NH— | pyrimidin-2-yl | mp. 243.2° C./ .2 HCl cis |
| 109 | 10 | H | H | CH₂ | —N(H)—(CH₂)₃—N(H)— | —C(=NH)—NH₂ | mp. 130.4° C. H₂SO₃ (1:1) |
| 110 | 10 | H | H | CH₂ | —N(CH₃)—(CH₂)₃—N(H)— | pyrimidin-2-yl | mp. 158.5° C. ethanedioate (1:1) |
| 111 | 10 | H | H | CH₂ | —N(H)—(CH₂)₃—N(H)— | 4,5,6,7-tetrahydro-1H-1,3-diazepin-2-yl | mp. 121.1° C. ethanedioate (1:2) |
| 112 | 10 | H | H | CH₂ | —N(H)—(CH₂)₃—N(H)— | 1-methyl-4,5-dihydro-1H-imidazol-2-yl | mp. 179.8° C./ ethanedioate (1:2) |
| 113 | 10 | H | H | CH₂ | —N(H)—(CH₂)₃—N(H)— | 5-cyanopyrimidin-2-yl | mp. 192.5° C. ethanedioate (1:1) |
| 114 | 10 | H | H | CH₂ | —N(H)—(CH₂)₃—N(H)— | 5-carbamoylpyrimidin-2-yl | mp. 127.8° C. |

TABLE 3-continued

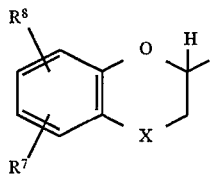

| Co. No. | Ex. No. | R⁷ | R⁸ | X | —CH₂—A | (C=N-R¹, N-R², R³) | physical data |
|---|---|---|---|---|---|---|---|
| 115 | 10 | H | H | CH₂ | —N(H)—(CH₂)₃—N(H)— | pyrazine | .HCl . ½ H₂O |
| 116 | 10 | 7-C₂H₅ | H | CH₂ | —N(H)—(CH₂)₃—N(H)— | 1,4-diazepane | mp. 219.8° C. ethanedioate (1:2) |
| 117 | 11 | H | H | CH₂ | —N(CH₃)—(CH₂)₂—N(CH₃)— | pyrazine | liquid |
| 118 | 11 | H | H | CH₂ | piperidin-4-yl-NH— | pyrazine | mp. 140.1° C./ (−) − (R) [α]$_D^{20}$ = −70.68° (c = 1% in CH₃OH) |
| 119 | 11 | H | H | CH₂ | —N(H)—CH(CH₃)—CH₂—N(H)— | pyrazine | mp. 150.2° C. ethanedioate (1:2) |
| 120 | 12 | H | H | CH₂ | —NH—CH₂— (piperidine) | pyrazine | mp. 246.6° C. ethanedioate (1:1) |
| 121 | 12 | H | H | CH₂ | CH₂—NH— (piperidine) | pyrazine | mp. 202.5° C./ . 2 HCl |
| 122 | 12 | H | H | CH₂ | —NH—(cyclohexane-1,4-diyl)—NH— | pyrazine | mp. 120.6° C. (B) |
| 123 | 12 | H | H | CH₂ | —NH—(cyclohexane-1,4-diyl)—NH— | pyrazine | mp. 254.9° C./.2 HCl (A) |

TABLE 3-continued

| Co. No. | Ex. No. | R⁷ | R⁸ | X | —CH₂—A | R³ | physical data |
|---|---|---|---|---|---|---|---|
| 124 | 13 | H | H | CH₂ | —N(H)—(CH₂)₃—N(CH₃)— | 1,4,5,6-tetrahydropyrimidin-2-yl | mp. 220.2° C. ethanedioate (1:2) |
| 125 | 14 | H | H | O | 1-(piperidin-4-yl)-N(CH₂CH₃)— | pyrimidin-2-yl | mp. 252.4° C. ethanedioate (1:1) |
| 126 | 14 | H | H | O | 1-(piperidin-4-yl)-N((CH₂)₃CH₃)— | pyrimidin-2-yl | mp. 218.1° C./ .2 HCl |
| 127 | 14 | H | H | O | 1-(piperidin-3-yl)-N(CH₃)— | pyrimidin-2-yl | mp. 205.4° C. .2HCl . 1/2 H₂O |
| 128 | 14 | H | H | CH₂ | 1-(piperidin-4-yl)-NH— | pyrimidin-2-yl | mp. 141.9° C. |
| 129 | 15 | H | H | CH₂ | —NH—(CH₂)₂—NH— | 4,5-dihydro-1H-imidazol-2-yl | mp. 226.0° C./. 2 HCl |
| 130 | 15 | H | H | CH₂ | —NH—(CH₂)₃—NH— | 4,5-dihydro-1H-imidazol-2-yl | mp. 165.8° C. . 2 HCl . H₂O |
| 131 | 15 | 6-F | H | CH₂ | 4,5-dihydro-1H-imidazol-2-yl | —NH—(CH₂)₂—NH— | mp. 242.1° C./ (−) − (R) . 2 HCl $[\alpha]_D^{20} = -72.75°$ (c = 1% in CH₃OH) |

TABLE 3-continued
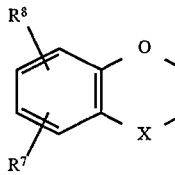
| Co. No. | Ex. No. | R⁷ | R⁸ | X | —CH₂—A | 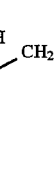 | physical data |
|---|---|---|---|---|---|---|---|
| 132 | 15 | H | H | CH₂ | —N—(CH₂)₃—N—<br>H　　　　H | 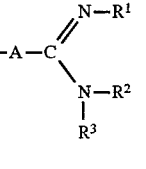 | mp. 254.0° C./ . 2. HCl |
| 133 | 15 | 7-C₂H₅ | H | CH₂ | —N—(CH₂)₃—N—<br>H　　　　H | 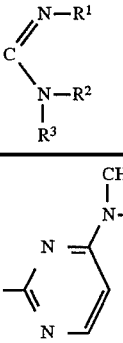 | mp. 199.2° C.<br>. 2 HCl . 1/2 H₂O |
| 134 | 15 | H | H | CH₂ | —N—(CH₂)₃—N—<br>H　　　　H | 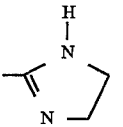 | mp. 190.6° C./<br>ethanedioate (1:2) |
| 135 | 15 | H | H | CH₂ | —N—(CH₂)₃—N—<br>H　　　　H | 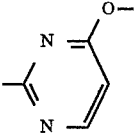 | mp. 190.3° C./<br>ethanedioate (1:2) |
| 136 | 16 | H | H | CH₂ | 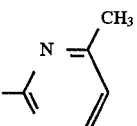 | 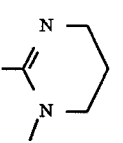 | mp. 239.8° C.<br>. 2 HCl .1/2 H₂O |
| 137 | 16 | H | H | CH₂ | 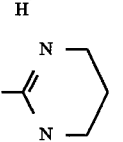 | 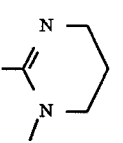 | mp. >300.0° C.<br>. 2 HCl |
| 138 | 16 | H | H | CH₂ | —N—(CH₂)₂—N—<br>CH₃　　　H | 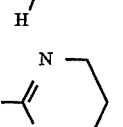 | mp. 172.7° C./ . 2 HCl |
| 139 | 16 | H | H | CH₂ | 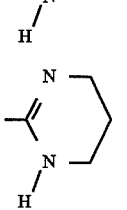 | 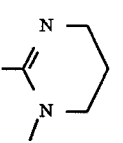 | mp. 230.0° C. (decom.)<br>[α]$_D^{20}$ = −57.20°<br><br>(c = 0.7% in CH₃OH) |

TABLE 3-continued

| Co. No. | Ex. No. | R⁷ | R⁸ | X | —CH₂—A | (amidine group) | physical data |
|---|---|---|---|---|---|---|---|
| | | | | | | | (−) − (R) · 2HCl · 3/2 H₂O |
| 140 | 16 | H | H | CH₂ | 1,3-cyclohexanediamine linker | tetrahydropyrimidine | mp. 175.9° C. · 2 HCl · 1/2 H₂O trans |
| 141 | 16 | H | H | CH₂ | 1,3-cyclohexanediamine linker | tetrahydropyrimidine | mp. 196.7° C. · 2 HCl · 1/2 H₂O cis |
| 142 | 16 | H | H | CH₂ | —NH—CH(CH₃)—CH₂—NH— | tetrahydropyrimidine | mp. 200.4° C. · 2 (COOH)₂ · 1/2 H₂O |
| 143 | 16 | H | H | CH₂ | —N(CH₃)—(CH₂)₃—NH— | tetrahydropyrimidine | mp. 158.2° C. ethanedioate (1:2) |
| 144 | 16 | H | H | CH₂ | 1,4-cyclohexanediamine linker | tetrahydropyrimidine | mp. 281.3° C. · 2 HCl trans |
| 145 | 16 | H | H | CH₂ | 1,4-cyclohexanediamine linker | tetrahydropyrimidine | mp. 273.1° C. · 2 HCl cis |
| 146 | 16 | H | H | CH₂ | piperidin-4-yl-CH₂—NH— | tetrahydropyrimidine | mp. 170.0° C. · 2 HCl · H₂O |
| 147 | 18 | 5-OH | H | CH₂ | —N(CH₃)—(CH₂)₃—NH— | pyrimidine | mp. 152.1° C. ethanedioate (1:2) |

TABLE 3-continued

| Co. No. | Ex. No. | R⁷ | R⁸ | X | —CH₂—A | $\underset{R^3}{\overset{N-R^1}{\underset{|}{\overset{\|}{C}}}}\!\!-\!\!N\!\!-\!\!R^2$ | physical data |
|---|---|---|---|---|---|---|---|
| 148 | 19 | H | H | CH₂ | —N(H)—(CH₂)₂—N(H)— | —C(=N—H)—NH—CH₂—CH₃ | mp. 235.1° C. .2 HCl . NH₄Cl |
| 149 | 19 | H | H | CH₂ | —N(H)—(CH₂)₃—N(H)— | —C(=N—H)—NH-n.C₃H₇ | mp. 149.9° C./ . 2 HCl |
| 150 | 19 | H | H | CH₂ | —N(H)—(CH₂)₃—N(H)— | —C(=N—H)—NH—CH(CH₃)₂ | mp. 97.5° C. . 2 HCl |
| 151 | 19 | H | H | CH₂ | —N(H)—(CH₂)₃—N(H)— | —C(=N—H)—N(CH₃)₂ | mp. 156.4° C./ . 2HCl . 1/2 (CH₃)₂CH—OH |
| 152 | 19 | 7-CH₃ | H | CH₂ | —N(H)—(CH₂)₃—N(H)— | —C(=N—H)—N(CH₃)₂ | mp. 224.4° C./ . 2 HCl |
| 153 | 19 | 7-C₂H₅ | H | CH₂ | —N(H)—(CH₂)₃—N(H)— | —C(=N—H)—N(CH₃)₂ | mp. 214.1° C. ethanedioate (1:2) |
| 154 | 19 | 7-C₂H₅ | H | CH₂ | —N(H)—(CH₂)₃—N(H)— | —C(=N—H)—NH—CH(CH₃)₂ | mp. 157.8° C. . 2 HCl. 1/2 H₂O |
| 155 | 20 | 6-F | H | CH₂ | —N(H)—(CH₂)₃—N(H)— | pyrimidinyl | mp. 228.2° C./ . HCl |

TABLE 4
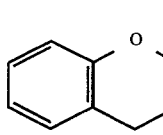
| Co. No. | Ex. No. | —CH₂—A | $\overset{N-R^2}{\underset{R^3}{C=N-R^1}}$ | physical data |
|---|---|---|---|---|
| 156 | 11 | 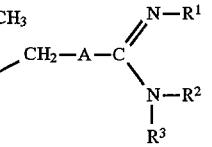 | 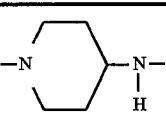 | — |
| 157 | 11 | —N(H)—(CH₂)₃—N(H)— | 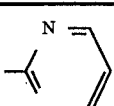 | mp. 105.8° C. . 2 HCl . 1/2 H₂O |
| 158 | 16 | 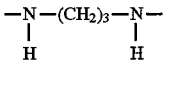 | 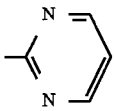 | mp. 242.0° C. . 2 HCl . 2 H₂O |
| 159 | 16 | —N(H)—(CH₂)₃—N(H)— | 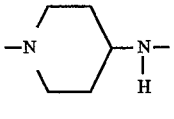 | mp. 229.4° C./ .2 HCl |
| 160 | 17 | —N(H)—(CH₂)₂—N(H)— | 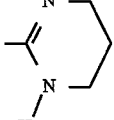 | liquid/ . 2 HCl . H₂O |
TABLE 5
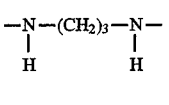
| Co. No. | Ex. No. | R⁷ | R⁸ | Alk¹ | $\overset{N-R^2}{\underset{R^3}{C=N-R^1}}$ | physical data |
|---|---|---|---|---|---|---|
| 161 | 10 | H | H | —(CH₂)₂— | 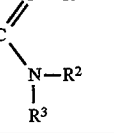 | mp. 188.6° C. ethanedioate (1:1) |

TABLE 5-continued

Structure: chroman with R8, R7 substituents, connected via Alk¹—NH—(CH₂)₃—NH—C(=N—R¹)(N(R³)—R²)

| Co. No. | Ex. No. | R⁷ | R⁸ | Alk¹ | R³ | physical data |
|---|---|---|---|---|---|---|
| 162 | 12 | 6-Br | H | —(CH₂)₃— | 2-pyrazinyl-methyl | mp. 191.7° C. ethanedioate (1:1) |
| 163 | 12 | H | H | —CH(CH₃)— | 2-pyrazinyl-methyl | mp. 183.0° C. (2S). HCl |
| 164 | 12 | H | H | —CH(CH₃)— | 2-pyrazinyl-methyl | mp. 182.1° C. (2R). HCl |
| 165 | 16 | H | H | —(CH₂)₃— | (1,4,5,6-tetrahydropyrimidin-2-yl)methyl | mp. 170.6° C. ethanedioate (1:2) |
| 166 | 16 | H | H | —(CH₂)₂— | (1,4,5,6-tetrahydropyrimidin-2-yl)methyl | mp. 193.5° C. ethanedioate (1:2) |
| 167 | 16 | H | H | —CH(CH₃)— | (1,4,5,6-tetrahydropyrimidin-2-yl)methyl | mp. 110.6° C. (2S). 2 HCl. 1/2 H₂O |
| 168 | 16 | H | H | —CH(CH₃)— | (1,4,5,6-tetrahydropyrimidin-2-yl)methyl | mp. 205.5° C. (2R). 2 HCl |

C. Pharmacological example

EXAMPLE 23

Segments of basilar aeries taken from pigs (anaesthetised with sodium pentobarbital) were mounted for recording of isometric tension in organ baths. The preparations were bathed in Krebs—Henseleit solution. The solution was kept at 37° C. and gassed with a mixture of 95% $O_2$-5% $CO_2$. The Preparations were stretched until a stable basal tension of 2 grams was obtained.

The preparations were made to constrict with serotonin ($3\times10^{-7}$ M). The response to the addition of serotonin was measured and subsequently the serotonin was washed away.

This Procedure was repeated until stable responses were obtained.

Subsequently the test compound was administered to the organ bath and the constriction of the Preparation was measured. This constrictive response is expressed as a Percentage of the response to serotonin as measured Previously.

The ED$_{50}$-value (molar concentration) is defined as the concentration at which a test compound causes 50% of the constrictive response obtained with serotonin. Said ED$_{50}$-values are estimated from experiments on three different preparations.

In table 6 the ED$_{50}$-values of compounds of formula (I) are presented.

TABLE 6

| Co. No. | ED$_{50}$ (M) |
| --- | --- |
| 3 | $1.46 \cdot 10^{-7}$ |
| 5 | $5.15 \cdot 10^{-7}$ |
| 13 | $4.22 \cdot 10^{-8}$ |
| 18 | $4.90 \cdot 10^{-8}$ |
| 46 | $1.00 \cdot 10^{-6}$ |
| 48 | $3.06 \cdot 10^{-7}$ |
| 56 | $1.87 \cdot 10^{-7}$ |
| 57 | $5.42 \cdot 10^{-7}$ |
| 62 | $3.17 \cdot 10^{-8}$ |
| 63 | $1.21 \cdot 10^{-7}$ |
| 64 | $8.97 \cdot 10^{-8}$ |
| 65 | $2.21 \cdot 10^{-7}$ |
| 66 | $6.56 \cdot 10^{-7}$ |
| 67 | $1.77 \cdot 10^{-8}$ |
| 68 | $3.33 \cdot 10^{-8}$ |
| 70 | $6.37 \cdot 10^{-9}$ |
| 72 | $2.34 \cdot 10^{-8}$ |
| 73 | $3.46 \cdot 10^{-9}$ |
| 76 | $9.19 \cdot 10^{-9}$ |
| 78 | $3.54 \cdot 10^{-8}$ |
| 82 | $1.76 \cdot 10^{-8}$ |
| 84 | $1.33 \cdot 10^{-8}$ |
| 86 | $4.16 \cdot 10^{-8}$ |
| 87 | $8.87 \cdot 10^{-8}$ |
| 88 | $7.02 \cdot 10^{-9}$ |
| 89 | $7.94 \cdot 10^{-8}$ |
| 95 | $8.17 \cdot 10^{-8}$ |
| 97 | $9.76 \cdot 10^{-8}$ |
| 98 | $3.42 \cdot 10^{-8}$ |
| 99 | $4.22 \cdot 10^{-8}$ |
| 106 | $3.90 \cdot 10^{-8}$ |
| 111 | $1.67 \cdot 10^{-8}$ |
| 113 | $1.63 \cdot 10^{-8}$ |
| 114 | $9.56 \cdot 10^{-8}$ |
| 115 | $4.51 \cdot 10^{-8}$ |
| 116 | $6.82 \cdot 10^{-8}$ |
| 129 | $4.44 \cdot 10^{-7}$ |
| 130 | $3.36 \cdot 10^{-8}$ |
| 133 | $5.27 \cdot 10^{-8}$ |
| 136 | $8.10 \cdot 10^{-7}$ |
| 139 | $1.50 \cdot 10^{-7}$ |
| 148 | $4.95 \cdot 10^{-7}$ |
| 149 | $9.92 \cdot 10^{-8}$ |
| 150 | $4.69 \cdot 10^{-8}$ |
| 151 | $2.71 \cdot 10^{-8}$ |
| 152 | $5.60 \cdot 10^{-8}$ |
| 153 | $2.18 \cdot 10^{-8}$ |

D. Composition Examples

"Active ingredient" (A.I.) as used throughout these examples relates to a compound of formula (I), a pharmaceutically acceptable acid addition salt or a stereochemically isomeric form thereof.

EXAMPLE 24: Oral Drops

500 Grams of the A.I. was dissolved in 0.5 l of 2-hydroxypropanoic acid and 1.5 l of the Polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 25: Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 26: Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE 27: Film-Coated Tablets

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.
Coating To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE 28: Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

EXAMPLE 29: Suppositories

3 Grams A.I. was dissolved in a solution of 3 grams 2,3-dihydroxybutanedioic acid in 25 ml polyethylene glycol 400. 12 Grams surfactant (SPAN®) and triglycerides (Witepsol 555®) q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

EXAMPLE 30: Injectable Solution

60 Grams of A.I. and 12 grams of benzylalcohol were mixed well and sesame oil was added q.s. ad 1 l, giving a solution comprising 60 mg/ml of A.I. The solution was sterilized and filled in sterile containers.

We claim:

1. A compound having the formula:

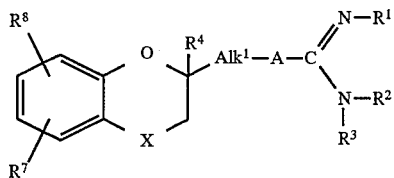

a pharmaceutically acceptable acid addition salt thereof, or a stereochemically isomeric form thereof, wherein:

X is O, $CH_2$ or a direct bond;

$R^1$ is hydrogen or $C_{1-6}$alkyl;

$R^2$ is hydrogen, $C_{1-6}$alkyl, $C_{3-6}$alkenyl or $C_{3-6}$alkynyl;

$R^3$ is hydrogen or $C_{1-6}$alkyl;

$R^4$ is hydrogen of $C_{1-6}$alkyl $Alk^1$ is a bivalent $C_{1-3}$alkanediyl radical;

A is a bivalent radical of the formula:

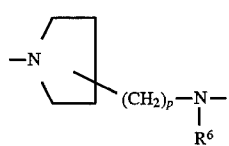

or

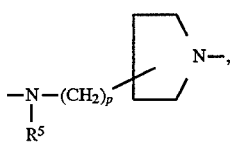

wherein:

$R^5$ and $R^6$ individually are hydrogen or $C_{1-4}$alkyl and p is 0, 1 or 2; and $R^7$ and $R^8$ each independently are hydrogen, halo, $C_{1-6}$alkyl, $C_{3-6}$alkenyl, $C_{3-6}$alkynyl, hydroxy, $C_{1-6}$alkyloxy, cyano, amino$C_{1-6}$alkyl, carboxyl, $C_{1-6}$alkyloxycarbonyl, nitro, amino, aminocarbonyl, $C_{1-6}$alkylcarbonylamino, or mono- or di($C_{1-6}$alkyl) amino.

2. A compound according to claim 1, wherein $Alk^1$ is $CH_2$.

3. A compound according to claim 1, wherein X is $CH_2$ and wherein $R^7$ and $R^8$ each independently are hydrogen, halo, $C_{1-6}$alkyl, $C_{1-6}$alkyloxy, hydroxy, cyano, nitro, amino$C_{1-6}$alkyl, amino, $C_{1-6}$alkylcarbonylamino.

4. A compound according to claim 2 wherein $R^6$ is hydrogen.

5. A compound according to claim 3 wherein $R^6$ is hydrogen.

6. A compound according to claim 4 wherein $R^5$ is hydrogen.

7. A compound according to claim 5 wherein $R^5$ is hydrogen.

8. A composition comprising a pharmaceutically acceptable carrier and as an active ingredient an effective vasoconstricting amount of a compound as defined in claim 1.

9. A composition comprising a pharmaceutically acceptable carrier and as an active ingredient an effective vasoconstricting amount of a compound as defined in claim 2.

10. A composition comprising a pharmaceutically acceptable carrier and as an active ingredient an effective vasoconstricting amount of a compound as defined in claim 3.

11. A composition comprising a pharmaceutically acceptable carrier and as an active ingredient an effective vasoconstricting amount of a compound as defined in claim 4.

12. A composition comprising a pharmaceutically acceptable carrier and as an active ingredient an effective vasoconstricting amount of a compound as defined in claim 5.

13. A composition comprising a pharmaceutically acceptable carrier and as an active ingredient an effective vasoconstricting amount of a compound as defined in claim 6.

14. A composition comprising a pharmaceutically acceptable carrier and as an active ingredient an effective vasoconstricting amount of a compound as defined in claim 7.

15. A method of treating migraine, which method comprises administering to patients in need of such treatment a therapeutically effective amount of a compound as defined in claim 1.

* * * * *